US005789568A

United States Patent [19]
Simons

[11] Patent Number: 5,789,568
[45] Date of Patent: Aug. 4, 1998

[54] HUMAN LEUKOCYTE ANTIGEN (HLA) LOCUS-SPECIFIC PRIMERS

[75] Inventor: Malcolm J. Simons, Fryerstown, Australia

[73] Assignee: GeneType A.G., Zug, Switzerland

[21] Appl. No.: 682,054

[22] Filed: Jul. 16, 1996

Related U.S. Application Data

[62] Division of Ser. No. 949,652, Sep. 23, 1992, which is a continuation of Ser. No. 551,239, Jul. 11, 1990, Pat. No. 5,192,659, which is a continuation-in-part of Ser. No. 465,863, Jan. 16, 1990, abandoned, which is a continuation-in-part of Ser. No. 405,499, Sep. 11, 1989, abandoned, which is a continuation-in-part of Ser. No. 398,217, Aug. 25, 1989, abandoned.

[51] Int. Cl.$^6$ ............ C07H 21/04; C12P 19/34; C12N 15/00
[52] U.S. Cl. ............ 536/24.33; 435/6; 435/91.2; 935/8
[58] Field of Search ............ 536/23.1, 24.1, 536/24.33, 25.3; 935/1, 8, 77, 76

[56] References Cited

PUBLICATIONS

New England BioLabs 1988–1989 Catalog, p. 62, 1988.
Search Report for nucleotide residue sequence "CTCTCAG-GCCTTGTT", Dec. 1996.

*Primary Examiner*—Bradley L. Sisson
*Attorney, Agent, or Firm*—McCutchen, Doyle, Brown & Enersen LLP

[57] ABSTRACT

The present invention provides a method for detection of at least one allele of a genetic locus and can be used to provide direct determination of the haplotype. The method comprises amplifying genomic DNA with a primer pair that spans an intron sequence and defines a DNA sequence in genetic linkage with an allele to be detected. The primer-defined DNA sequence contains a sufficient number of intron sequence nucleotides to characterize the allele. Genomic DNA is amplified to produce an amplified DNA sequence characteristic of the allele. The amplified DNA sequence is analyzed to detect the presence of a genetic variation in the amplified DNA sequence such as a change in the length of the sequence, gain or loss of a restriction site or substitution of a nucleotide. The variation is characteristic of the allele to be detected and can be used to detect remote alleles. Kits comprising one or more of the reagents used in the method are also described.

1 Claim, No Drawings

HUMAN LEUKOCYTE ANTIGEN (HLA) LOCUS-SPECIFIC PRIMERS

CROSS REFERENCE TO RELATED APPLICATION

This application is a division of application Ser. No. 07/949,652, filed Sep. 23, 1992, which is a continuation of application Ser. No. 07/551,239, filed Jul. 11, 1990, now U.S. Pat. No. 5,192,659 issued Mar. 9, 1993, which is a continuation-in-part of application Ser. No. 07/465,863, filed Jan. 16, 1990 (now abandoned), which is a continuation-in-part of application Ser. No. 07/405,499, filed Sep. 11, 1989 (now abandoned), which is a continuation-in-part of application Ser. No. 07/398,217, filed Aug. 25, 1989 (now abandoned).

FIELD OF THE INVENTION

The present invention relates to a method for detection of alleles and haplotypes and reagents therefor.

BACKGROUND OF THE INVENTION

Due in part to a number of new analytical techniques, there has been a significant increase in knowledge about genetic information, particularly in humans. Allelic variants of genetic loci have been correlated to malignant and non-malignant monogenic and multigenic diseases. For example, monogenic diseases for which the defective gene has been identified include DuChenne muscular dystrophy, sickle-cell anemia, Lesch Nyhan syndrome, hemophilia, beta-thalassemia, cystic fibrosis, polycystic kidney disease, ADA deficiency, α-1-antitrypsin deficiency, Wilm's tumor and retinoblastoma. Other diseases which are believed to be monogenic for which the gene has not been identified include fragile X mental retardation and Huntington's chorea.

Genes associated with multigenic diseases such as diabetes, colon cancer and premature coronary atherosclerosis have also been identified.

In addition to identifying individuals at risk for or carriers of genetic diseases, detection of allelic variants of a genetic locus has been used for organ transplantation, forensics, disputed paternity and a variety of other purposes in humans. In commercially important plants and animals, genes have not only been analyzed but genetically engineered and transmitted into other organisms.

A number of techniques have been employed to detect allelic variants of genetic loci including analysis of restriction fragment length polymorphic (RFLP) patterns, use of oligonucleotide probes, and DNA amplification methods. One of the most complicated groups of allelic variants, the major histocompatibility complex (MHC), has been extensively studied. The problems encountered in attempting to determine the HLA type of an individual are exemplary of problems encountered in characterizing other genetic loci.

The major histocompatibility complex is a cluster of genes that occupy a region on the short arm of chromosome 6. This complex, denoted the human leukocyte antigen (HLA) complex, includes at least 50 loci. For the purposes of HLA tissue typing, two main classes of loci are recognized. The Class I loci encode transplantation antigens and are designated A, B and C. The Class II loci (DRA, DRB, DQA1, DQB, DPA and DPB) encode products that control immune responsiveness. Of the Class II loci, all the loci are polymorphic with the exception of the DRA locus. That is, the DRa antigen polypeptide sequence is invariant.

HLA determinations are used in paternity determinations, transplant compatibility testing, forensics, blood component therapy, anthropological studies, and in disease association correlations to diagnose disease or predict disease susceptibility. Due power of HLA to distinguish individuals and the need to match HLA type for transplantation, analytical methods to unambiguously characterize the alleles of the genetic loci associated with the complex have been sought. At present, DNA typing using RFLP and oligonucleotide probes has been used to type Class II locus alleles. Alleles of Class I loci and Class II DR and DQ loci are typically determined by serological methods. The alleles of the Class II DP locus are determined by primed lymphocyte typing (PLT).

Each of the HLA analysis methods has drawbacks. Serological methods require standard sera that are not widely available and must be continuously replenished. Additionally, serotyping is based on the reaction of the HLA gene products in the sample with the antibodies in the reagent sera. The antibodies recognize the expression products of the HLA genes on the surface of nucleated cells. The determination of fetal HLA type by serological methods may be difficult due to lack of maturation of expression of the antigens in fetal blood cells.

Oligonucleotide probe typing can be performed in two days and has been further improved by the recent use of polymerase chain reaction (PCR) amplification. PCR-based oligoprobe typing has been performed on Class II loci. Primed lymphocyte typing requires 5 to 10 days to complete and involves cell culture with its difficulties and inherent variability.

RFLP analysis is time consuming, requiring about 5 to 7 days to complete. Analysis of the fragment patterns is complex. Additionally, the technique requires the use of labelled probes. The most commonly used label, $^{32}P$, presents well known drawbacks associated with the use of radionuclides.

A fast, reliable method of genetic locus analysis is highly desirable.

DESCRIPTION OF THE PRIOR ART

U.S. Pat. No. 4,683,195 (to Mullis et al. issued Jul. 28, 1987) describes a process for amplifying, detecting and/or cloning nucleic acid sequences. The method involves treating separate complementary strands of DNA with two oligonucleotide primers, extending the primers to form complementary extension products that act as templates for synthesizing the desired nucleic acid sequence and detecting the amplified sequence. The method is commonly referred to as the polymerase chain reaction sequence amplification method or PCR. Variations of the method are described in U.S. Pat. No. 4,683,194 (to Saiki et al. issued Jul. 28, 1987). The polymerase chain reaction sequence amplification method is also described by Saiki et al, Science, 230:1350–1354 (1985) and Scharf et al, Science, 324:163–166 (1986).

U.S. Pat. No. 4,582,788 (to Erlich, issued Apr. 15, 1986) describes an HLA typing method based on restriction length polymorphism (RFLP) and cDNA probes used therewith. The method is carried out by digesting an individual's HLA DNA with a restriction endonuclease that produces a polymorphic digestion pattern, subjecting the digest to genomic blotting using a labelled cDNA probe that is complementary to an HLA DNA sequence involved in the polymorphism, and comparing the resulting genomic blotting pattern with a standard. Locus-specific probes for Class II loci (DQ) are also described.

Kogan et al. *New Engl. J. Med*, 317:985–990 (1987) describes an improved PCR sequence amplification method that uses a heat-stable polymerase (Taq polymerase) and high temperature amplification. The stringent conditions used in the method provide sufficient fidelity of replication to permit analysis of the amplified DNA by determining DNA sequence lengths by visual inspection of an ethidium bromide-stained gel. The method was used to analyze DNA associated with hemophilia A in which additional tandem repeats of a DNA sequence are associated with the disease and the amplified sequences were significantly longer than sequences that are not associated with the disease.

Simons and Erlich, pp 952–958 In: *Immunology of HLA* Vol. 1: Springer-Verlag, New York (1989) summarized RFLP-sequence interrelations at the DPA and DPB loci. RFLP fragment patterns analyzed with probes by Southern blotting provided distinctive patterns for DPw1-5 alleles and the corresponding DPB1 allele sequences, characterized two subtypic patterns for DPw2 and DPw4, and identified new DPw alleles.

Simons et al, pp 959–1023 In: *Immunology of HLA* Vol. 1: Springer-Verlag, New York (1989) summarized restriction length polymorphisms of HLA sequences for class II loci as determined by the 10th International Workshop Southern Blot Analysis. Southern blot analysis was shown to be suitable for typing of the major classes of HLA loci.

A series of three articles [Rommens et al, *Science* 245:1059–1065 (1989), Riordan et al, *Science* 245:1066–1072 (1989) and Kerem et al, *Science* 245:1073–1079 (1989) report a new gene analysis method called "jumping" used to identify the location of the CF gene, the sequence of the CF gene, and the defect in the gene and its percentage in the disease population, respectively.

DiLelia et al, *The Lancet* i:497–499 (1988) describes a screening method for detecting the two major alleles responsible for phenylketonuria in Caucasians of Northern European descent. The mutations, located at about the center of exon 12 and at the exon 12 junction with intervening sequence 12 are detected by PCR amplification of a 245 bp region of exon 12 and flanking intervening sequences. The amplified sequence encompasses both mutations and is analyzed using probes specific for each of the alleles (without prior electrophoretic separation).

Dicker et al, *BioTechniques* 7:830–837 (1989) and Mardis et al, *BioTechniques* 7:840–850 (1989) report on automated techniques for sequencing of DNA sequences, particularly PCR-generated sequences.

Each of the above-described references is incorporated herein by reference in its entirety.

SUMMARY OF THE INVENTION

The present invention provides a method for detection of at least one allele of a genetic locus and can be used to provide direct determination of the haplotype. The method comprises amplifying genomic DNA with a primer pair that spans an intron sequence and defines a DNA sequence in genetic linkage with an allele to be detected. The primer-defined DNA sequence contains a sufficient number of intron sequence nucleotides to characterize the allele. Genomic DNA is amplified to produce an amplified DNA sequence characteristic of the allele. The amplified DNA sequence is analyzed to detect the presence of a genetic variation in the amplified DNA sequence such as a change in the length of the sequence, gain or loss of a restriction site or substitution of a nucleotide. The variation is characteristic of the allele to be detected.

The present invention is based on the finding that intron sequences contain genetic variations that are characteristic of adjacent and remote alleles on the same chromosome. In particular, DNA sequences that include a sufficient number of intron sequence nucleotides can be used for direct determination of haplotype.

The method can be used to detect alleles of genetic loci for any eukaryotic organism. Of particular interest are loci associated with malignant and nonmalignant monogenic and multigenic diseases, and identification of individual organisms or species in both plants and animals. In a preferred embodiment, the method is used to determine HLA allele type and haplotype.

Kits comprising one or more of the reagents used in the method are also described.

DETAILED DESCRIPTION OF THE INVENTION

The present invention provides a method for detection of alleles and haplotypes through analysis of intron sequence variation. The present invention is based on the discovery that amplification of intron sequences that exhibit linkage disequilibrium with adjacent and remote loci can be used to detect alleles of those loci. The present method reads haplotypes as the direct output of the intron typing analysis when a single, individual organism is tested. The method is particularly useful in humans but is generally applicable to all eukaryotes, and is preferably used to analyze plant and animal species.

The method comprises amplifying genomic DNA with a primer pair that spans an intron sequence and defines a DNA sequence in genetic linkage with an allele to be detected. Primer sites are located in conserved regions in the introns or exons bordering the intron sequence to be amplified. The primer-defined DNA sequence contains a sufficient number of intron sequence nucleotides to characterize the allele. The amplified DNA sequence is analyzed to detect the presence of a genetic variation such as a change in the length of the sequence, gain or loss of a restriction site or substitution of a nucleotide.

The intron sequences provide genetic variations that, in addition to those found in exon sequences, further distinguish sample DNA, providing additional information about the individual organism. This information is particularly valuable for identification of individuals such as in paternity determinations and in forensic applications. The information is also valuable in any other application where heterozygotes (two different alleles) are to be distinguished from homozygotes (two copies of one allele).

More specifically, the present invention provides information regarding intron variation. Using the methods and reagents of this invention, two types of intron variation associated with genetic loci have been found. The first is allele-associated intron variation. That is, the intron variation pattern associates with the allele type at an adjacent locus. The second type of variation is associated with remote alleles (haplotypes). That is, the variation is present in individual organisms with the same genotype at the primary locus. Differences may occur between sequences of the same adjacent and remote locus types. However, individual-limited variation is uncommon.

Furthermore, an amplified DNA sequence that contains sufficient intron sequences will vary depending on the allele present in the sample. That is, the introns contain genetic variations (e.g. length polymorphisms due to insertions and/or deletions and changes in the number or location of restriction sites) which are associated with the particular allele of the locus and with the alleles at remote loci.

The reagents used in carrying out the methods of this invention are also described. The reagents can be provided in kit form comprising one or more of the reagents used in the method.

Definitions

The term "allele", as used herein, means a genetic variation associated with a coding region; that is, an alternative form of the gene.

The term "linkage", as used herein, refers to the degree to which regions of genomic DNA are inherited together. Regions on different chromosomes do not exhibit linkage and are inherited together 50% of the time. Adjacent genes that are always inherited together exhibit 100% linkage.

The term "linkage disequilibrium", as used herein, refers to the co-occurrence of two alleles at linked loci such that the frequency of the co-occurrence of the alleles is greater than would be expected from the separate frequencies of occurrence of each allele. Alleles that co-occur with frequencies expected from their separate frequencies are said to be in "linkage equilibrium".

As used herein, "haplotype" is a region of genomic DNA on a chromosome which is bounded by recombination sites such that genetic loci within a haplotypic region are usually inherited as a unit. However, occasionally, genetic rearrangements may occur within a haplotype. Thus, the term haplotype is an operational term that refers to the occurrence on a chromosome of linked loci.

As used herein, the term "intron" refers to untranslated DNA sequences between exons, together with 5' and 3' untranslated regions associated with a genetic locus. In addition, the term is used to refer to the spacing sequences between genetic loci (intergenic spacing sequences) which are not associated with a coding region and are colloquially referred to as "junk". While the art traditionally uses the term "intron" to refer only to untranslated sequences between exons, this expanded definition was necessitated by the lack of any art recognized term which encompasses all non-exon sequences.

As used herein, an "intervening sequence" is an intron which is located between two exons within a gene. The term does not encompass upstream and downstream noncoding sequences associated with the genetic locus.

As used herein, the term "amplified DNA sequence" refers to DNA sequences which are copies of a portion of a DNA sequence and its complementary sequence, which copies correspond in nucleotide sequence to the original DNA sequence and its complementary sequence.

The term "complement", as used herein, refers to a DNA sequence that is complementary to a specified DNA sequence.

The term "primer site", as used herein, refers to the area of the target DNA to which a primer hybridizes.

The term "primer pair", as used herein, means a set of primers including a 5' upstream primer that hybridizes with the 5' end of the DNA sequence to be amplified and a 3' downstream primer that hybridizes with the complement of the 3' end of the sequence to be amplified.

The term "exon-limited primers", as used herein, means a primer pair having primers located within or just outside of an exon in a conserved portion of the intron, which primers amplify a DNA sequence which includes an exon or a portion thereof and not more than a small, para-exon region of the adjacent intron(s).

The term "intron-spanning primers", as used herein, means a primer pair that amplifies at least a portion of one intron, which amplified intron region includes sequences which are not conserved. The intron-spanning primers can be located in conserved regions of the introns or in adjacent, upstream and/or downstream exon sequences.

The term "genetic locus", as used herein, means the region of the genomic DNA that includes the gene that encodes a protein including any upstream or downstream transcribed noncoding regions and associated regulatory regions. Therefore, an HLA locus is the region of the genomic DNA that includes the gene that encodes an HLA gene product.

As used herein, the term "adjacent locus" refers to either (1) the locus in which a DNA sequence is located or (2) the nearest upstream or downstream genetic locus for intron DNA sequences not associated with a genetic locus.

As used herein, the term "remote locus" refers to either (1) a locus which is upstream or downstream from the locus in which a DNA sequence is located or (2) for intron sequences not associated with a genetic locus, a locus which is upstream or downstream from the nearest upstream or downstream genetic locus to the intron sequence.

The term "locus-specific primer", as used herein, means a primer that specifically hybridizes with a portion of the stated gene locus or its complementary strand, at least for one allele of the locus, and does not hybridize with other DNA sequences under the conditions used in the amplification method.

As used herein, the terms "endonuclease" and "restriction endonuclease" refer to an enzyme that cuts double-stranded DNA having a particular nucleotide sequence. The specificities of numerous endonucleases are well known and can be found in a variety of publications, e.g. *Molecular Cloning: A Laboratory Manual* by Maniatis et al, Cold Spring Harbor Laboratory 1982. That manual is incorporated herein by reference in its entirety.

The term "restriction fragment length polymorphism" (or RFLP), as used herein, refers to differences in DNA nucleotide sequences that produce fragments of different lengths when cleaved by a restriction endonuclease.

The term "primer-defined length polymorphisms" (or PDLP), as used herein, refers to differences in the lengths of amplified DNA sequences due to insertions or deletions in the intron region of the locus included in the amplified DNA sequence.

The term "HLA DNA", as used herein, means DNA that includes the genes that encode HLA antigens. HLA DNA is found in all nucleated human cells.

Primers

The method of this invention is based on amplification of selected intron regions of genomic DNA. The methodology is facilitated by the use of primers that selectively amplify DNA associated with one or more alleles of a genetic locus of interest and not with other genetic loci.

A locus-specific primer pair contains a 5' upstream primer that defines the 5' end of the amplified sequence by hybridizing with the 5' end of the target sequence to be amplified and a 3' downstream primer that defines the 3' end of the amplified sequence by hybridizing with the complement of the 3' end of the DNA sequence to be amplified. The primers in the primer pair do not hybridize with DNA of other genetic loci under the conditions used in the present invention.

For each primer of the locus-specific primer pair, the primer hybridizes to at least one allele of the DNA locus to be amplified or to its complement. A primer pair can be prepared for each allele of a selected locus, which primer pair amplifies only DNA for the selected locus. In this way combinations of primer pairs can be used to amplify genomic DNA of a particular locus, irrespective of which allele is present in a sample. Preferably, the primer pair amplifies DNA of at least two, more preferably more than two, alleles of a locus. In a most preferred embodiment, the primer sites are conserved, and thus amplify all haplotypes. However, primer pairs or combinations thereof that specifically bind with the most common alleles present in a particular population group are also contemplated.

The amplified DNA sequence that is defined by the primers contains a sufficient number of intron sequence nucleotides to distinguish between at least two alleles of an adjacent locus, and preferably, to identify the allele of the locus which is present in the sample. For some purposes, the sequence can also be selected to contain sufficient genetic variations to distinguish between individual organisms with the same allele or to distinguish between haplotypes.

Length of Sequence

The length of the amplified sequence which is required to include sufficient genetic variability to enable discrimination between all alleles of a locus bears a direct relation to the extent of the polymorphism of the locus (the number of alleles). That is, as the number of alleles of the tested locus increases, the size of an amplified sequence which contains sufficient genetic variations to identify each allele increases. For a particular population group, one or more of the recognized alleles for any given locus may be absent from that group and need not be considered in determining a sequence which includes sufficient variability for that group. Conveniently, however, the primer pairs are selected to amplify a DNA sequence which is sufficient to distinguish between all recognized alleles of the tested locus. The same considerations apply when a haplotype is determined.

For example, the least polymorphic HLA locus is DPA which currently has four recognized alleles. For that locus, a primer pair which amplifies only a portion of the variable exon encoding the allelic variation contains sufficient genetic variability to distinguish between the alleles when the primer sites are located in an appropriate region of the variable exon. Exon-limited primers can be used to produce an amplified sequence that includes as few as about 200 nucleotides (nt). However, as the number of alleles of the locus increases, the number of genetic variations in the sequence must increase to distinguish all alleles. Addition of invariant exon sequences provides no additional genetic variation. When about eight or more alleles are to be distinguished, as for the DQA1 locus and more variable loci, amplified sequences should extend into at least one intron in the locus, preferably an intron adjacent to the variable exon.

Additionally, where alleles of the locus exist which differ by a single basepair in the variable exon, intron sequences are included in amplified sequences to provide sufficient variability to distinguish alleles. For example, for the DQA1 locus (with eight currently recognized alleles) and the DPB locus (with 24 alleles), the DQA1.1/1.2 (now referred to as DQA1 0101/0102) and DPB2.1/4.2 (now referred to as DPB0201/0402) alleles differ by a single basepair. To distinguish those alleles, amplified sequences which include an intron sequence region are required. About 300 to 500 nucleotides is sufficient, depending on the location of the sequence. That is, 300 to 500 nucleotides comprised primarily of intron sequence nucleotides sufficiently close to the variable exon are sufficient.

For loci with more extensive polymorphisms (such as DQB with 14 currently recognized alleles, DPB with 24 currently recognized alleles, DRB with 34 currently recognized alleles and for each of the Class I loci), the amplified sequences need to be larger to provide sufficient variability to distinguish between all the alleles. An amplified sequence that includes at least about 0.5 kilobases (Kb), preferably at least about 1.0 Kb, more preferably at least about 1.5 Kb generally provides a sufficient number of restriction sites for loci with extensive polymorphisms. The amplified sequences used to characterize highly polymorphic loci are generally between about 800 to about 2,000 nucleotides (nt), preferably between about 1000 to about 1800 nucleotides in length.

When haplotype information regarding remote alleles is desired, the sequences are generally between about 1,000 to about 2,000 nt in length. Longer sequences are required when the amplified sequence encompasses highly conserved regions such as exons or highly conserved intron regions, e.g., promoters, operators and other DNA regulatory regions. Longer amplified sequences (including more intron nucleotide sequences) are also required as the distance between the amplified sequences and the allele to be detected increases.

Highly conserved regions included in the amplified DNA sequence, such as exon sequences or highly conserved intron sequences (e.g. promoters, enhancers, or other regulatory regions) may provide little or no genetic variation. Therefore, such regions do not contribute, or contribute only minimally, to the genetic variations present in the amplified DNA sequence. When such regions are included in the amplified DNA sequence, additional nucleotides may be required to encompass sufficient genetic variations to distinguish alleles, in comparison to an amplified DNA sequence of the same length including only intron sequences.

Location of the Amplified DNA Sequence

The amplified DNA sequence is located in a region of genomic DNA that contains genetic variation which is in genetic linkage with the allele to be detected. Preferably, the sequence is located in an intron sequence adjacent to an exon of the genetic locus. More preferably, the amplified sequence includes an intervening sequence adjacent to an exon that encodes the allelic variability associated with the locus (a variable exon). The sequence preferably includes at least a portion of one of the introns adjacent to a variable exon and can include a portion of the variable exon. When additional sequence information is required, the amplified DNA sequence preferably encompasses a variable exon and all or a portion of both adjacent intron sequences.

Alternatively, the amplified sequence can be in an intron which does not border an exon of the genetic locus. Such introns are located in the downstream or upstream gene flanking regions or even in an intervening sequence in another genetic locus which is in linkage disequilibrium with the allele to be detected.

For some genetic loci, genomic DNA sequences may not be available. When only cDNA sequences are available and intron locations within the sequence are not identified, primers are selected at intervals of about 200 nt and used to amplify genomic DNA. If the amplified sequence contains about 200 nt, the location of the first primer is moved about 200 nt to one side of the second primer location and the amplification is repeated until either (1) an amplified DNA sequence that is larger than expected is produced or (2) no amplified DNA sequence is produced. In either case, the location of an intron sequence has been determined. The same methodology can be used when only the sequence of a marker site that is highly linked to the genetic locus is available, as is the case for many genes associated with inherited diseases.

When the amplified DNA sequence does not include all or a portion of an intron adjacent to the variable exon(s), the sequence must also satisfy a second requirement. The amplified sequence must be sufficiently close to the variable exon(s) to exclude recombination and loss of linkage disequilibrium between the amplified sequence and the variable exon(s). This requirement is satisfied if the regions of the genomic DNA are within about 5 Kb, preferably within about 4 Kb, most preferably within 2 Kb of the variable exon(s). The amplified sequence can be outside of the genetic locus but is preferably within the genetic locus.

Preferably, for each primer pair, the amplified DNA sequence defined by the primers includes at least 200 nucleotides, and more preferably at least 400 nucleotides, of an intervening sequence adjacent to the variable exon(s). Although the variable exon usually provides fewer variations in a given number of nucleotides than an adjacent intervening sequence, each of those variations provides allele-relevant information. Therefore, inclusion of the variable exon provides an advantage.

Since PCR methodology can be used to amplify sequences of several Kb, the primers can be located so that additional exons or intervening sequences are included in the amplified sequence. Of course, the increased size of the amplified DNA sequence increases the chance of replication error, so addition of invariant regions provides some disadvantages. However, those disadvantages are not as likely to affect an analysis based on the length of the sequence or the RFLP fragment patterns as one based on sequencing the amplification product. For particular alleles, especially those with highly similar exon sequences, amplified sequences of greater than about 1 or 1.5 Kb may be necessary to discriminate between all alleles of a particular locus.

The ends of the amplified DNA sequence are defined by the primer pair used in the amplification. Each primer sequence must correspond to a conserved region of the genomic DNA sequence. Therefore, the location of the amplified sequence will, to some extent, be dictated by the need to locate the primers in conserved regions. When sufficient intron sequence information to determine conserved intron regions is not available, the primers can be located in conserved portions of the exons and used to amplify intron sequences between those exons.

When appropriately-located, conserved sequences are not unique to the genetic locus, a second primer located within the amplified sequence produced by the first primer pair can be used to provide an amplified DNA sequence specific for the genetic locus. At least one of the primers of the second primer pair is located in a conserved region of the amplified DNA sequence defined by the first primer pair. The second primer pair is used following amplification with the first primer pair to amplify a portion of the amplified DNA sequence produced by the first primer pair.

There are three major types of genetic variations that can be detected and used to identify an allele. Those variations, in order of ease of detection, are (1) a change in the length of the sequence, (2) a change in the presence or location of at least one restriction site and (3) the substitution of one or a few nucleotides that does not result in a change in a restriction site. Other variations within the amplified DNA sequence are also detectable.

There are three types of techniques which can be used to detect the variations. The first is sequencing the amplified DNA sequence. Sequencing is the most time consuming and also the most revealing analytical method, since it detects any type of genetic variation in the amplified sequence. The second analytical method uses allele-specific oligonucleotide or sequence-specific oligonucleotides probes (ASO or SSO probes). Probes can detect single nucleotide changes which result in any of the types of genetic variations, so long as the exact sequence of the variable site is known. A third type of analytical method detects sequences of different lengths (e.g., due to an insertion or deletion or a change in the location of a restriction site) and/or different numbers of sequences (due to either gain or loss of restriction sites). A preferred detection method is by gel or capillary electrophoresis. To detect changes in the lengths of fragments or the number of fragments due to changes in restriction sites, the amplified sequence must be digested with an appropriate restriction endonuclease prior to analysis of fragment length patterns.

The first genetic variation is a difference in the length of the primer-defined amplified DNA sequence, referred to herein as a primer-defined length polymorphism (PDLP), which difference in length distinguishes between at least two alleles of the genetic locus. The PDLPs result from insertions or deletions of large stretches (in comparison to the total length of the amplified DNA sequence) of DNA in the portion of the intron sequence defined by the primer pair. To detect PDLPs, the amplified DNA sequence is located in a region containing insertions or deletions of a size that is detectable by the chosen method. The amplified DNA sequence should have a length which provides optimal resolution of length differences. For electrophoresis, DNA sequences of about 300 to 500 bases in length provide optimal resolution of length differences. Nucleotide sequences which differ in length by as few as 3 nt, preferably 25 to 50 nt, can be distinguished. However, sequences as long as 800 to 2,000 nt which differ by at least about 50 nt are also readily distinguishable. Gel electrophoresis and capillary electrophoresis have similar limits of resolution. Preferably the length differences between amplified DNA sequences will be at least 10, more preferably 20, most preferably 50 or more, nt between the alleles. Preferably, the amplified DNA sequence is between 300 to 1,000 nt and encompasses length differences of at least 3, preferably 10 or more nt.

Preferably, the amplified sequence is located in an area which provides PDLP sequences that distinguish most or all of the alleles of a locus. An example of PDLP-based identification of five of the eight DQA1 alleles is described in detail in the examples.

When the variation to be detected is a change in a restriction site, the amplified DNA sequence necessarily contains at least one restriction site which (1) is present in one allele and not in another, (2) is apparently located in a different position in the sequence of at least two alleles, or (3) combinations thereof. The amplified sequence will preferably be located such that restriction endonuclease cleavage produces fragments of detectably different lengths, rather than two or more fragments of approximately the same length.

For allelic differences detected by ASO or SSO probes, the amplified DNA sequence includes a region of from about 200 to about 400 nt which is present in one or more alleles and not present in one or more other alleles. In a most preferred embodiment, the sequence contains a region detectable by a probe that is present in only one allele of the genetic locus. However, combinations of probes which react with some alleles and not others can be used to characterize the alleles.

For the method described herein, it is contemplated that use of more than one amplified DNA sequence and/or use of more than one analytical method per amplified DNA sequence may be required for highly polymorphic loci, particularly for loci where alleles differ by single nucleotide substitutions that are not unique to the allele or when information regarding remote alleles (haplotypes) is desired. More particularly, it may be necessary to combine a PDLP analysis with an RFLP analysis, to use two or more amplified DNA sequences located in different positions or to digest a single amplified DNA sequence with a plurality of endonucleases to distinguish all the alleles of some loci. These combinations are intended to be included within the scope of this invention.

For example, the analysis of the haplotypes of DQA1 locus described in the examples uses PDLPs and RFLP analysis using three different enzyme digests to distinguish the eight alleles and 20 of the 32 haplotypes of the locus.

Length and Sequence Homology of Primers

Each locus-specific primer includes a number of nucleotides which, under the conditions used in the hybridization, are sufficient to hybridize with an allele of the locus to be amplified and to be free from hybridization with alleles of other loci. The specificity of the primer increases with the number of nucleotides in its sequence under conditions that provide the same stringency. Therefore, longer primers are desirable. Sequences with fewer than 15 nucleotides are less certain to be specific for a particular locus. That is, sequences with fewer than 15 nucleotides are more likely to be present in a portion of the DNA associated with other genetic loci, particularly loci of other common origin or evolutionarily closely related origin, in inverse proportion to the length of the nucleotide sequence.

Each primer preferably includes at least about 15 nucleotides, more preferably at least about 20 nucleotides. The primer preferably does not exceed about 30 nucleotides, more preferably about 25 nucleotides. Most preferably, the primers have between about 20 and about 25 nucleotides.

A number of preferred primers are described herein. Each of those primers hybridizes with at least about 15 consecutive nucleotides of the designated region of the allele sequence. For many of the primers, the sequence is not identical for all of the other alleles of the locus. For each of the primers, additional preferred primers have sequences which correspond to the sequences of the homologous region of other alleles of the locus or to their complements.

When two sets of primer pairs are used sequentially, with the second primer pair amplifying the product of the first primer pair, the primers can be the same size as those used for the first amplification. However, smaller primers can be used in the second amplification and provide the requisite specificity. These smaller primers can be selected to be allelespecific, if desired. The primers of the second primer pair can have 15 or fewer, preferably 8 to 12, more preferably 8 to 10 nucleotides. When two sets of primer pairs are used to produce two amplified sequences, the second amplified DNA sequence is used in the subsequent analysis of genetic variation and must meet the requirements discussed previously for the amplified DNA sequence.

The primers preferably have a nucleotide sequence that is identical to a portion of the DNA sequence to be amplified or its complement. However, a primer having two nucleotides that differ from the target DNA sequence or its complement also can be used. Any nucleotides that are not identical to the sequence or its complement are preferably not located at the 3' end of the primer. The 3' end of the primer preferably has at least two, preferably three or more, nucleotides that are complementary to the sequence to which the primer binds. Any nucleotides that are not identical to the sequence to be amplified or its complement will preferably not be adjacent in the primer sequence. More preferably, noncomplementary nucleotides in the primer sequence will be separated by at least three, more preferably at least five, nucleotides. The primers should have a melting temperature ($T_m$) from about 55° to 75° C. Preferably the $T_m$ is from about 60° C. to about 65° C. to facilitate stringent amplification conditions.

The primers can be prepared using a number of methods, such as, for example, the phosphotriester and phosphodiester methods or automated embodiments thereof. The phosphodiester and phosphotriester methods are described in Cruthers, *Science* 230:281–285 (1985); Brown et al, *Meth. Enzymol.*, 68:109 (1979); and Nrang et al, *Meth. Enzymol.*, 68:90 (1979). In one automated method, diethylphosphoramidites which can be synthesized as described by Beaucage et al, *Tetrahedron letters*, 22:1859–1962 (1981) are used as starting materials. A method for synthesizing primer oligonucleotide sequences on a modified solid support is described in U.S. Pat. No. 4,458,066. Each of the above references is incorporated herein by reference in its entirety.

Exemplary primer sequences for analysis of Class I and Class II HLA loci; bovine leukocyte antigens, and cystic fibrosis are described herein.

Amplification

The locus-specific primers are used in an amplification process to produce a sufficient amount of DNA for the analysis method. For production of RFLP fragment patterns or PDLP patterns which are analyzed by electrophoresis, about 1 to about 500 ng of DNA is required. A preferred amplification method is the polymerase chain reaction (PCR). PCR amplification methods are described in U.S. Pat. No. 4,683,195 (to Mullis et al, issued Jul. 28, 1987); U.S Pat. No. 4,683,194 (to Saiki et al, issued Jul. 28, 1987); Saiki et al, *Science*, 230:1350–1354 (1985); Scharf et al, *Science*, 324:163–166 (1986); Kogan et al, *New Engl. J. Med*, 317:985–990 (1987) and Saiki, Gyllensten and Erlich, *The Polymerase Chain Reaction in Genome Analysis: A Practical Approach*, ed. Davies pp. 141–152, (1988) I.R.L. Press, Oxford. Each of the above references is incorporated herein by reference in its entirety.

Prior to amplification, a sample of the individual organism's DNA is obtained. All nucleated cells contain genomic DNA and, therefore, are potential sources of the required DNA. For higher animals, peripheral blood cells are typically used rather than tissue samples. As little as 0.01 to 0.05 cc of peripheral blood provides sufficient DNA for amplification. Hair, semen and tissue can also be used as samples. In the case of fetal analyses, placental cells or fetal cells present in amniotic fluid can be used. The DNA is isolated from nucleated cells under conditions that minimize DNA degradation. Typically, the isolation involves digesting the cells with a protease that does not attack DNA at a temperature and pH that reduces the likelihood of DNase activity. For peripheral blood cells, lysing the cells with a hypotonic solution (water) is sufficient to release the DNA.

DNA isolation from nucleated cells is described by Kan et al, *N. Engl. J. Med.* 297:1080–1084 (1977); Kan et al, *Nature* 251:392–392 (1974); and Kan et al, PNAS 75:5631–5635 (1978). Each of the above references is incorporated herein by reference in its entirety. Extraction procedures for samples such as blood, semen, hair follicles, semen, mucous membrane epithelium and other sources of genomic DNA are well known. For plant cells, digestion of the cells with cellulase releases DNA. Thereafter DNA is purified as described above.

The extracted DNA can be purified by dialysis, chromatography, or other known methods for purifying polynucleotides prior to amplification. Typically, the DNA is not purified prior to amplification.

The amplified DNA sequence is produced by using the portion of the DNA and its complement bounded by the primer pair as a template. As a first step in the method, the DNA strands are separated into single stranded DNA. This strand separation can be accomplished by a number of methods including physical or chemical means. A preferred method is the physical method of separating the strands by heating the DNA until it is substantially (approximately 93%) denatured. Heat denaturation involves temperatures ranging from about 80° to 105° C. for times ranging from about 15 to 30 seconds. Typically, heating the DNA to a temperature of from 90° to 93° C. for about 30 seconds to about 1 minute is sufficient.

The primer extension product(s) produced are complementary to the primer-defined region of the DNA and hybridize therewith to form a duplex of equal length strands. The duplexes of the extension products and their templates are then separated into single-stranded DNA. When the complementary strands of the duplexes are separated, the strands are ready to be used as a template for the next cycle of synthesis of additional DNA strands.

Each of the synthesis steps can be performed using conditions suitable for DNA amplification. Generally, the amplification step is performed in a buffered aqueous solution, preferably at a pH of about 7 to about 9, more preferably about pH 8. A suitable amplification buffer contains Tris-HCl as a buffering agent in the range of about 10 to 100 mM. The buffer also includes a monovalent salt, preferably at a concentration of at least about 10 mM and not greater than about 60 mM. Preferred monovalent salts are KCl, NaCl and $(NH_4)_2SO_4$. The buffer also contains $MgCl_2$ at about 5 to 50 mM. Other buffering systems such as hepes or glycine-NaOH and potassium phosphate buffers can be used. Typically, the total volume of the amplification reaction mixture is about 50 to 100 μl.

Preferably, for genomic DNA, a molar excess of about $10^6$:1 primer:template of the primer pair is added to the buffer containing the separated DNA template strands. A large molar excess of the primers improves the efficiency of the amplification process. In general, about 100 to 150 ng of each primer is added.

The deoxyribonucleotide triphosphates dATP, dCTP, dGTP and dTTP are also added to the amplification mixture in amounts sufficient to produce the amplified DNA sequences. Preferably, the dNTPs are present at a concentration of about 0.75 to about 4.0 mM, more preferably about 2.0 mM. The resulting solution is heated to about 90° to 93° C. for from about 30 seconds to about 1 minute to separate the strands of the DNA. After this heating period the solution is cooled to the amplification temperature.

Following separation of the DNA strands, the primers are allowed to anneal to the strands. The annealing temperature varies with the length and GC content of the primers. Those variables are reflected in the $T_m$ of each primer. Exemplary HLA DQA1 primers of this invention, described below, require temperatures of about 55° C. The exemplary HLA Class I primers of this invention require slightly higher temperatures of about 62° to about 68° C. The extension reaction step is performed following annealing of the primers to the genomic DNA.

An appropriate agent for inducing or catalyzing the primer extension reaction is added to the amplification mixture either before or after the strand separation (denaturation) step, depending on the stability of the agent under the denaturation conditions. The DNA synthesis reaction is allowed to occur under conditions which are well known in the art. This synthesis reaction (primer extension) can occur at from room temperature up to a temperature above which the polymerase no longer functions efficiently. Elevating the amplification temperature enhances the stringency of the reaction. As stated previously, stringent conditions are necessary to ensure that the amplified sequence and the DNA template sequence contain the same nucleotide sequence, since substitution of nucleotides can alter the restriction sites or probe binding sites in the amplified sequence.

The inducing agent may be any compound or system which facilitates synthesis of primer extension products, preferably enzymes. Suitable enzymes for this purpose include DNA polymerases (such as, for example, *E. coli* DNA polymerase I, Klenow fragment of *E. coli* DNA polymerase I, T4 DNA polymerase), reverse transcriptase, and other enzymes (including heat-stable polymerases) which facilitate combination of the nucleotides in the proper manner to form the primer extension products. Most preferred is Taq polymerase or other heat-stable polymerases which facilitate DNA synthesis at elevated temperatures (about 60° to 90° C.). Taq polymerase is described, e.g., by Chien et al. *J. Bacteriol.*, 127:1550–1557 (1976). That article is incorporated herein by reference in its entirety. When the extension step is performed at about 72° C., about 1 minute is required for every 1000 bases of target DNA to be amplified.

The synthesis of the amplified sequence is initiated at the 3' end of each primer and proceeds toward the 5' end of the template along the template DNA strand, until synthesis terminates, producing DNA sequences of different lengths. The newly synthesized strand and its complementary strand form a double-stranded molecule which is used in the succeeding steps of the process. In the next step, the strands of the double-stranded molecule are separated (denatured) as described above to provide single-stranded molecules.

New DNA is synthesized on the single-stranded template molecules. Additional polymerase, nucleotides and primers can be added if necessary for the reaction to proceed under the conditions described above. After this step, half of the extension product consists of the amplified sequence bounded by the two primers. The steps of strand separation and extension product synthesis can be repeated as many times as needed to produce the desired quantity of the amplified DNA sequence. The amount of the amplified sequence produced accumulates exponentially. Typically, about 25 to 30 cycles are sufficient to produce a suitable amount of the amplified DNA sequence for analysis.

The amplification method can be performed in a step-wise fashion where after each step new reagents are added, or simultaneously, where all reagents are added at the initial step, or partially step-wise and partially simultaneously, where fresh reagent is added after a given number of steps. The amplification reaction mixture can contain, in addition to the sample genomic DNA, the four nucleotides, the primer pair in molar excess, and the inducing agent, e.g., Taq polymerase.

Each step of the process occurs sequentially notwithstanding the initial presence of all the reagents. Additional materials may be added as necessary. Typically, the polymerase is not replenished when using a heat-stable polymerase. After the appropriate number of cycles to produce the desired amount of the amplified sequence, the reaction may be halted by inactivating the enzymes, separating the components of the reaction or stopping the thermal cycling.

In a preferred embodiment of the method, the amplification includes the use of a second primer pair to perform a second amplification following the first amplification. The second primer pair defines a DNA sequence which is a portion of the first amplified sequence. That is, at least one of the primers of the second primer pair defines one end of the second amplified sequence which is within the ends of the first amplified sequence. In this way, the use of the second primer pair helps to ensure that any amplified sequence produced in the second amplification reaction is specific for the tested locus. That is, non-target sequences which may be copied by a locus-specific pair are unlikely to contain sequences that hybridize with a second locus-specific primer pair located within the first amplified sequence.

In another embodiment, the second primer pair is specific for one allele of the locus. In this way, detection of the presence of a second amplified sequence indicates that the allele is present in the sample. The presence of a second amplified sequence can be determined by quantitating the amount of DNA at the start and the end of the second amplification reaction. Methods for quantitating DNA are well known and include determining the optical density at 260 ($OD_{260}$), and preferably additionally determining the ratio of the optical density at 260 to the optical density at 280 ($OD_{260}/OD_{280}$) to determine the amount of DNA in comparison to protein in the sample.

Preferably, the first amplification will contain sufficient primer for only a limited number of primer extension cycles, e.g. less than 15, preferably about 10 to 12 cycles, so that the amount of amplified sequence produced by the process is sufficient for the second amplification but does not interfere with a determination of whether amplification occurred with the second primer pair. Alternatively, the amplification reaction can be continued for additional cycles and aliquoted to provide appropriate amounts of DNA for one or more second amplification reactions. Approximately 100 to 150 ng of each primer of the second primer pair is added to the amplification reaction mixture. The second set of primers is preferably added following the initial cycles with the first primer pair. The amount of the first primer pair can be limited in comparison to the second primer pair so that, following addition of the second pair, substantially all of the amplified sequences will be produced by the second pair.

As stated previously, the DNA can be quantitated to determine whether an amplified sequence was produced in the second amplification. If protein in the reaction mixture interferes with the quantitation (usually due to the presence of the polymerase), the reaction mixture can be purified, as by using a 100,000 MW cut off filter. Such filters are commercially available from Millipore and from Centricon.

Analysis of the Amplified DNA Sequence

As discussed previously, the method used to analyze the amplified DNA sequence to characterize the allele(s) present in the sample DNA depends on the genetic variation in the sequence. When distinctions between alleles include primer-defined length polymorphisms, the amplified sequences are separated based on length, preferably using gel or capillary electrophoresis. When using probe hybridization for analysis, the amplified sequences are reacted with labeled probes. When the analysis is based on RFLP fragment patterns, the amplified sequences are digested with one or more restriction endonucleases to produce a digest and the resultant fragments are separated based on length, preferably using gel or capillary electrophoresis. When the only variation encompassed by the amplified sequence is a sequence variation that does not result in a change in length or a change in a restriction site and is unsuitable for detection by a probe, the amplified DNA sequences are sequenced.

Procedures for each step of the various analytical methods are well known and are described below.

Production of RFLP Fragment Patterns
Restriction Endonucleases

A restriction endonuclease is an enzyme that cleaves or cuts DNA hydrolytically at a specific nucleotide sequence called a restriction site. Endonucleases that produce blunt end DNA fragments (hydrolysis of the phosphodiester bonds on both DNA strands occur at the same site) as well as endonucleases that produce sticky ended fragments (the hydrolysis sites on the strands are separated by a few nucleotides from each other) can be used.

Restriction enzymes are available commercially from a number of sources including Sigma Pharmaceuticals, Bethesda Research Labs, Boehringer-Manheim and Pharmacia. As stated previously, a restriction endonuclease used in the present invention cleaves an amplified DNA sequence of this invention to produce a digest comprising a set of fragments having distinctive fragment lengths. In particular, the fragments for one allele of a locus differ in size from the fragments for other alleles of the locus. The patterns produced by separation and visualization of the fragments of a plurality of digests are sufficient to distinguish each allele of the locus. More particularly, the endonucleases are chosen so that by using a plurality of digests of the amplified sequence, preferably fewer than five, more preferably two or three digests, the alleles of a locus can be distinguished.

In selecting an endonuclease, the important consideration is the number of fragments produced for amplified sequences of the various alleles of a locus. More particularly, a sufficient number of fragments must be produced to distinguish between the alleles and, if required, to provide for individuality determinations. However, the number of fragments must not be so large or so similar in size that a pattern that is not distinguishable from those of other haplotypes by the particular detection method is produced. Preferably, the fragments are of distinctive sizes for each allele. That is, for each endonuclease digest of a particular amplified sequence, the fragments for an allele preferably differ from the fragments for every other allele of the locus by at least 10, preferably 20, more preferably 30, most preferably 50 or more nucleotides.

One of ordinary skill can readily determine whether an endonuclease produces RFLP fragments having distinctive fragment lengths. The determination can be made experimentally by cleaving an amplified sequence for each allele with the designated endonuclease in the invention method. The fragment patterns can then be analyzed. Distinguishable patterns will be readily recognized by determining whether comparison of two or more digest patterns is sufficient to demonstrate characteristic differences between the patterns of the alleles.

The number of digests that need to be prepared for any particular analysis will depend on the desired information and the particular sample to be analyzed. Since HLA analyses are used for a variety of purposes ranging from individuality determinations for forensics and paternity to tissue typing for transplantation, the HLA complex will be used as exemplary.

A single digest may be sufficient to determine that an individual cannot be the person whose blood was found at a crime scene. In general, however, where the DNA samples do not differ, the use of two to three digests for each of two to three HLA loci will be sufficient for matching applications (forensics, paternity). For complete HLA typing, each locus needs to be determined.

In a preferred embodiment, sample HLA DNA sequences are divided into aliquots containing similar amounts of DNA per aliquot and are amplified with primer pairs (or combinations of primer pairs) to produce amplified DNA sequences for a number of HLA loci. Each amplification mixture contains only primer pairs for one HLA locus. The amplified sequences are preferably processed concurrently, so that a number of digest RFLP fragment patterns can be produced from one sample. In this way, the HLA type for a number of alleles can be determined simultaneously.

Alternatively, preparation of a number of RFLP fragment patterns provides additional comparisons of patterns to distinguish samples for forensic and paternity analyses where analysis of one locus frequently fails to provide sufficient information for the determination when the sample DNA has the same allele as the DNA to which it is compared.

Production of RFLP Fragments

Following amplification, the amplified DNA sequence is combined with an endonuclease that cleaves or cuts the amplified DNA sequence hydrolytically at a specific restriction site. The combination of the endonuclease with the amplified DNA sequence produces a digest containing a set of fragments having distinctive fragment lengths. U.S. Pat. No. 4,582,788 (to Erlich, issued Apr. 15, 1986) describes an HLA typing method based on restriction length polymorphism (RFLP). That patent is incorporated herein by reference in its entirety.

In a preferred embodiment, two or more aliquots of the amplification reaction mixture having approximately equal amounts of DNA per aliquot are prepared. Conveniently about 5 to about 10 µl of a 100 µl reaction mixture is used for each aliquot. Each aliquot is combined with a different endonuclease to produce a plurality of digests. In this way, by using a number of endonucleases for a particular amplified DNA sequence, locus-specific combinations of endonucleases that distinguish a plurality of alleles of a particular locus can be readily determined. Following preparation of the digests, each of the digests can be used to form RFLP patterns. Preferably, two or more digests can be pooled prior to pattern formation.

Alternatively, two or more restriction endonucleases can be used to produce a single digest. The digest differs from one where each enzyme is used separately and the resultant fragments are pooled since fragments produced by one enzyme may include one or more restriction sites recognized by another enzyme in the digest. Patterns produced by simultaneous digestion by two or more enzymes will include more fragments than pooled products of separate digestions using those enzymes and will be more complex to analyze.

Furthermore, one or more restriction endonucleases can be used to digest two or more amplified DNA sequences. That is, for more complete resolution of all the alleles of a locus, it may be desirable to produce amplified DNA sequences encompassing two different regions. The amplified DNA sequences can be combined and digested with at least one restriction endonuclease to produce RFLP patterns.

The digestion of the amplified DNA sequence with the endonuclease can be carried out in an aqueous solution under conditions favoring endonuclease activity. Typically the solution is buffered to a pH of about 6.5 to 8.0. Mild temperatures, preferably about 20° C. to about 45° C., more preferably physiological temperatures (25° to 40° C.), are employed. Restriction endonucleases normally require magnesium ions and, in some instances, cofactors (ATP and S-adenosyl methionine) or other agents for their activity. Therefore, a source of such ions, for instance inorganic magnesium salts, and other agents, when required, are present in the digestion mixture. Suitable conditions are described by the manufacturer of the endonuclease and generally vary as to whether the endonuclease requires high, medium or low salt conditions for optimal activity.

The amount of DNA in the digestion mixture is typically in the range of 1% to 20% by weight. In most instances 5 to 20 µg of total DNA digested to completion provides an adequate sample for production of RFLP fragments. Excess endonuclease, preferably one to five units/µg DNA, is used.

The set of fragments in the digest is preferably further processed to produce RFLP patterns which are analyzed. If desired, the digest can be purified by precipitation and resuspension as described by Kan et al, *PNAS* 75:5631–5635 (1978), prior to additional processing. That article is incorporated herein by reference in its entirety.

Once produced, the fragments are analyzed by well known methods. Preferably, the fragments are analyzed using electrophoresis. Gel electrophoresis methods are described in detail hereinafter. Capillary electrophoresis methods can be automated (as by using Model 207A analytical capillary electrophoresis system from Applied Biosystems of Foster City, Calif.) and are described in Chin et al, *American Biotechnology Laboratory News Edition*, Dec., 1989.

Electrophoretic Separation of DNA Fragments

Electrophoresis is the separation of DNA sequence fragments contained in a supporting medium by size and charge under the influence of an applied electric field. Gel sheets or slabs, e.g. agarose, agarose-acrylamide or polyacrylamide, are typically used for nucleotide sizing gels. The electrophoresis conditions affect the desired degree of resolution of the fragments. A degree of resolution that separates fragments that differ in size from one another by as little as 10 nucleotides is usually sufficient. Preferably, the gels will be capable of resolving fragments which differ by 3 to 5 nucleotides. However, for some purposes (where the differences in sequence length are large), discrimination of sequence differences of at least 100 nt may be sufficiently sensitive for the analysis.

Preparation and staining of analytical gels is well known. For example, a 3% Nusieve 1% agarose gel which is stained using ethidium bromide is described in Boerwinkle et al, *PNAS*, 86:212–216 (1989). Detection of DNA in polyacrylamide gels using silver stain is described in Goldman et al, *Electrophoresis*, 3:24–26 (1982); Marshall, *Electrophoresis*, 4:269–272 (1983); Tegelstrom, *Electrophoresis*, 7:226–229 (1987); and Allen et al, *BioTechniques* 7:736–744 (1989). The method described by Allen et al, using large-pore size ultrathin-layer, rehydratable polyacrylamide gels stained with silver is preferred. Each of those articles is incorporated herein by reference in its entirety.

Size markers can be run on the same gel to permit estimation of the size of the restriction fragments. Comparison to one or more control sample(s) can be made in addition to or in place of the use of size markers. The size markers or control samples are usually run in one or both the lanes at the edge of the gel, and preferably, also in at least one central lane. In carrying out the electrophoresis, the DNA fragments are loaded onto one end of the gel slab (commonly called the "origin") and the fragments separate by electrically facilitated transport through the gel, with the shortest fragment electrophoresing from the origin towards the other (anode) end of the slab at the fastest rate. An agarose slab gel is typically electrophoresed using about 100 volts for 30 to 45 minutes. A polyacrylamide slab gel is typically electrophoresed using about 200 to 1,200 volts for 45 to 60 minutes.

After electrophoresis, the gel is readied for visualization. The DNA fragments can be visualized by staining the gel with a nucleic acid-specific stain such as ethidium bromide or, preferably, with silver stain, which is not specific for DNA. Ethidium bromide staining is described in Boerwinkle et al, supra. Silver staining is described in Goldman et al, supra, Marshall, supra, Tegelstrom, supra, and Allen et al, supra.

Probes

Allele-specific oligonucleotides or probes are used to identify DNA sequences which have regions that hybridize with the probe sequence. The amplified DNA sequences defined by a locus-specific primer pair can be used as probes in RFLP analyses using genomic DNA. U.S. Pat. No. 4,582,788 (to Erlich, issued Apr. 15, 1986) describes an exemplary HLA typing method based on analysis of RFLP patterns produced by genomic DNA. The analysis uses cDNA probes to analyze separated DNA fragments in a Southern blot type of analysis. As stated in the patent "[C]omplementary DNA probes that are specific to one (locus-specific) or more (multilocus) particular HLA DNA sequences involved in the polymorphism are essential components of the hybridization step of the typing method" (col. 6, 1. 3–7).

The amplified DNA sequences of the present method can be used as probes in the method described in that patent or in the present method to detect the presence of an amplified DNA sequence of a particular allele. More specifically, an amplified DNA sequence having a known allele can be produced and used as a probe to detect the presence of the allele in sample DNA which is amplified by the present method.

Preferably, however, when a probe is used to distinguish alleles in the amplified DNA sequences of the present invention, the probe has a relatively short sequence (in comparison to the length of the amplified DNA sequence) which minimizes the sequence homology of other alleles of the locus with the probe sequence. That is, the probes will correspond to a region of the amplified DNA sequence which has the largest number of nucleotide differences from the amplified DNA sequences of other alleles produced using that primer pair.

The probes can be labelled with a detectable atom, radical or ligand using known labeling techniques. Radiolabels, usually $^{32}$P, are typically used. The probes can be labeled with $^{32}$P by nick translation with an α-$^{32}$P-dNTP (Rigby et al, J. Mol. Biol., 113:237 (1977)) or other available procedures to make the locus-specific probes for use in the methods described in the patent. The probes are preferably labeled with an enzyme, such as hydrogen peroxidase. Coupling enzyme labels to nucleotide sequences are well known. Each of the above references is incorporated herein by reference in its entirety.

The analysis method known as "Southern blotting" that is described by Southern, J. Mol. Biol., 98:503–517 (1975) is an analysis method that relies on the use of probes. In Southern blotting the DNA fragments are electrophoresed, transferred and affixed to a support that binds nucleic acid, and hybridized with an appropriately labeled cDNA probe. Labeled hybrids are detected by autoradiography, or preferably, use of enzyme labels.

Reagents and conditions for blotting are described by Southern, supra; Wahl et al, PNAS 6:3683–3687 (1979); Kan et al, PNAS, supra, U.S. Pat. No. 4:302,204 and Molecular Cloning: A Laboratory Manual by Maniatis et al, Cold Spring Harbor Laboratory 1982. After the transfer is complete the paper is separated from the gel and is dried. Hybridization (annealing) of the resolved single stranded DNA on the paper to an probe is effected by incubating the paper with the probe under hybridizing conditions. See Southern, supra; Kan et al, PNAS, supra and U.S. Pat. No. 4,302,204, col 5, line 8 et seq. Complementary DNA probes specific for one allele, one locus (locus-specific) or more are essential components of the hybridization step of the typing method. Locus-specific probes can be made by the amplification method for locus-specific amplified sequences, described above. The probes are made detectable by labeling as described above.

The final step in the Southern blotting method is identifying labeled hybrids on the paper (or gel in the solution hybridization embodiment). Autoradiography can be used to detect radiolabel-containing hybrids. Enzyme labels are detected by use of a color development system specific for the enzyme. In general, the enzyme cleaves a substrate, which cleavage either causes the substrate to develop or change color. The color can be visually perceptible in natural light or a fluorochrome which is excited by a known wavelength of light.

Sequencing

Genetic variations in amplified DNA sequences which reflect allelic difference in the sample DNA can also be detected by sequencing the amplified DNA sequences. Methods for sequencing oligonucleotide sequences are well known and are described in, for example, Molecular Cloning: A Laboratory Manual by Maniatis et al, Cold Spring Harbor Laboratory 1982. Currently, sequencing can be automated using a number of commercially available instruments.

Due to the amount of time currently required to obtain sequencing information, other analysis methods, such as gel electrophoresis of the amplified DNA sequences or a restriction endonuclease digest thereof are preferred for clinical analyses.

Kits

As stated previously, the kits of this invention comprise one or more of the reagents used in the above described methods. In one embodiment, a kit comprises at least one genetic locus-specific primer pair in a suitable container. Preferably the kit contains two or more locus-specific primer pairs. In one embodiment, the primer pairs are for different loci and are in separate containers. In another embodiment, the primer pairs are specific for the same locus. In that embodiment, the primer pairs will preferably be in the same container when specific for different alleles of the same genetic locus and in different containers when specific for different portions of the same allele sequence. Sets of primer pairs which are used sequentially can be provided in separate containers in one kit. The primers of each pair can be in separate containers, particularly when one primer is used in each set of primer pairs. However, each pair is preferably provided at a concentration which facilitates use of the primers at the concentrations required for all amplifications in which it will be used.

The primers can be provided in a small volume (e.g. 100 μl) of a suitable solution such as sterile water or Tris buffer and can be frozen. Alternatively, the primers can be air dried.

In another embodiment, a kit comprises, in separate containers, two or more endonucleases useful in the methods of this invention. The kit will preferably contain a locus-specific combination of endonucleases. The endonucleases can be provided in a suitable solution such as normal saline or physiologic buffer with 50% glycerol (at about −20° C.) to maintain enzymatic activity.

The kit can contain one or more locus-specific primer pairs together with locus-specific combinations of endonucleases and may additionally include a control. The control can be an amplified DNA sequence defined by a locus-specific primer pair or DNA having a known HLA type for a locus of interest.

Additional reagents such as amplification buffer, digestion buffer, a DNA polymerase and nucleotide triphosphates can be provided separately or in the kit. The kit may additionally contain gel preparation and staining reagents or preformed gels.

Analyses of exemplary genetic loci are described below.

Analysis of HLA Type

The present method of analysis of genetic variation in an amplified DNA sequence to determine allelic difference in sample DNA can be used to determine HLA type. Primer pairs that specifically amplify genomic DNA associated with one HLA locus are described in detail hereinafter. In a preferred embodiment, the primers define a DNA sequence that contains all exons that encode allelic variability associated with the HLA locus together with at least a portion of one of the adjacent intron sequences. For Class I loci, the variable exons are the second and third exons. For Class II loci, the variable exon is the second exon. The primers are preferably located so that a substantial portion of the amplified sequence corresponds to intron sequences.

The intron sequences provide restriction sites that, in comparison to cDNA sequences, provide additional information about the individual; e.g., the haplotype. Inclusion of exons within the amplified DNA sequences does not provide as many genetic variations that enable distinction between alleles as an intron sequence of the same length, particularly for constant exons. This additional intron sequence information is particularly valuable in paternity determinations and in forensic applications. It is also valuable in typing for transplant matching in that the variable lengths of intron sequences included in the amplified sequence produced by the primers enables a distinction to be made between certain heterozygotes (two different alleles) and homozygotes (two copies of one allele).

Allelic differences in the DNA sequences of HLA loci are illustrated below. The tables illustrate the sequence homology of various alleles and indicate exemplary primer binding sites. Table 1 is an illustration of the alignment of the nucleotides of the Class I A2, A3, Ax, A24 (formerly referred to as A9), B27, B58 (formerly referred to as B17), C1, C2 and C3 allele sequences in intervening sequence (IVS) I and III. (The gene sequences and their numbering that are used in the tables and throughout the specification can be found in the Genbank and/or European Molecular Biology Laboratories (EMBL) sequence databanks. Those sequences are incorporated herein by reference in their entirety.) Underlined nucleotides represent the regions of the sequence to which exemplary locus-specific or Class I-specific primers bind.

Table 2 illustrates the alignment of the nucleotides in IVS I and II of the DQA3 (now DQA1 0301), DQA1.2 (now DQA1 0102) and DQA4.1 (now DQA1 0501) alleles of the DQA1 locus (formerly referred to as the DR4, DR6 and DR3 alleles of the DQA1 locus, respectively). Underlined nucleotides represent the regions of the sequence to which exemplary DQA1 locus-specific primers bind.

Table 3 illustrates the alignment of the nucleotides in IVS I, exon 2 and IVS II of two individuals having the DQw1$_y$ allele (designated hereinafter as DQw1,a and DQw1,b for the upper and lower sequences in the table, respectively), the DQw2 and DQw8 alleles of the DQB1 locus. Nucleotides indicated in the DQw1,b, DQw2 and DQw8 allele sequences are those which differ from the DQw1,a sequence. Exon 2 begins and ends at nt 599 and nt 870 of the DQw1,a allele sequence, respectively. Underlined nucleotides represent the regions of the sequence to which exemplary DQB1 locus-specific primers bind.

Table 4 illustrates the alignment of the nucleotides in IVS I, exon 2 and IVS II of the DPB4.1, DPB9, New and DPw3 alleles of the DPB1 locus. Nucleotides indicated in the DPB9, New and DPw3 allele sequences are those which differ from the DPB4.1 sequence. Exon 2 begins and ends at nt 7644 and nt 7907 of the DPB4.1 allele sequence, respectively. Underlined nucleotides represent the regions of the sequence to which exemplary DPB1 locus-specific primers bind.

TABLE I

| Class I Seq | | |
|---|---|---|
| C1 | 1 | GATTACCAATATTGTGCGACCTACTGTATCAATAAAC |
| C2 | 1 | T |
| C1 | 38 | AAAAAGGAAACTGGTCTCTATGAGAATCTCTACCTGGTGCTTTCAGACAA |
| C2 | 38 | G G |
| C1 | 88 | CACTTCACCAGGTTTAAAGAGAAAACTCCTGACTCTACACGTCCATTCCC |
| C2 | 88 | |
| B27 | 1 | GAGCTCACTCTCTGGCATCAAGTTC          TCCGTG |
| C1 | 138 | AGGGCGAGCTCACTGTCTGGCAGCAAGTTCCCCATGGTCGAGTTTCCCTG |
| C2 | 138 | T                − |

TABLE I-continued

```
Class I Seq

A2    1    AAGCTTACTCTCTGGCACCAAAC  TCCATGGGATGATTTTTCCTTCC TAG
B27   32                                                      ATCAGTTTCCCT
C1    188  TACAAGAGTCCAAGGGGAGAGGTAAGTGTCCTTT    AT    TTTGCTGGATGTAG
C2    187

A2    50        AAGAGTCCAGGTGGACAGGTAA  GGAGTGGGAGT           CAGGGAGTC
B27   44   ACACAAGA TCCAAGAGGAGAGGTAA  GGAGT    GAG      AGGCAGGGAGTC
C1    238  TTTAATATTACCT GAGGTAAGGTAA  GGC AAAGAGTGGG  AGGCAGGGAGTC
C2    237                                 C    -                G

A2    98   CAGTTCCAGGGACAGAGATTACGGGATAAAAAGTGAAAGGAGAGGGACG    GGGCCCAT
B27   91   CAGTT CAGGGACAGGGATTCCAGGAGGAGAAGTGAAGGGGAAGC  GGG TGGGC
C1    288  CAGTT CAGGGACGGGGATTCCAGGAGAAG     TGAAGGGGAAG  GGGCTGGGCG
C2    288                                                            -

A2    149      GCCGAG    GGTTTCTCCCTTGTTTCT CAGACAGCTC TTGGGCCA A GAC
B27   141      GCCACTGGGGGTCTCTCCCTGGTTTCCACAGACAGATCCTTGTGCC        GGAC
C1    338  CAGCC  TGGGGGTCTCTCCCTGGTTTCCACAGACAGATCCTTG GCC    AGGAC
C2    337                                                     - -  GG

A2    195  TCAGGGAGACATTGAGACAGAGC GCTTGGCACAGAAGCAGAGGGGTCAGGG
B27   191  TCAGGCAGACAGTGTGACAAAGAGGCT GGTGTAGGAGAAGAGGGATCAGG
C1    388  TCAGGCACACAGTGTGACAAAGATGCTTGGTGTAGGAGAAGAGGGATCAG
C2    387                                                      G

A2    246  CGAA GTCCAGGGCCCCAGGCGTTGGCTCTCAGGGTCTCAGGCCCCGAAGG
A3    1
Ax    1
A24   1
B27   241  ACGAACGTCCAAGGCCCCGGGCG CGG TCTCAGGGTCTCAGGCTCCGAGAG
C1    438  ACGAA GTCCCAGGTCCCGGGCG GGGTTCTCAGGGTCTCAGGCTCCAAGGG
C2    438            -A

A2    296  CGGTGTATGGATTGGGGAGTCCCAGCCTTGGGGATTCCCCAACTCCGC AGTT
A3    9        T      A                -
Ax    9               TG                           G  C
A24   11                                         -    - T
B27   291  CCTTGTCTGCATTGGGGAGGCGCACAGTTGGGG TTCCCCACTCCCACGAGTT
C1    488  CCGTGTCTGCACTGGGGAGGCGCCGCGTTGAGGATTCTCCACTCCCCTGA
C2    488

A2    348  TCTTTTCTCCC  TCTCCCAACCTATGTAGGGTCCTTCTTCCTGGAT ACTCAC
A3    60              CTG        C            A                  G
Ax    61    C     ---      A    GC AC               C
A24   61              TG-                      -
B27   344  TCACTTCT      TCTCCCAACCTATGTCGGGTCCTTCTTCCAGGAT ACTCGT
C1    538    G TTCACTTCTTCTCCCAACCTGCGTCGGGTCCTTCTTCCTGAAT ACTCAT
C2    538    T                      A
C3    1                              T G                     G

A2    399  GACGCGGACCCAGTTCTCACTCCCATTGGGTGTCGGGTTTCC    AGAGAAG C
A3    114
Ax    109    A     A     T    C A                   - T
A24   111                                            G
B27   392  GACGCGTCCCCATTTC CACTCCCATTGGGTGTCGGGT    GTCTAGAGAAG C
B58   1
C1    588  GACGCGTCCCCAATTCCCACTCCCATTGGGTGTCGGGT    TCT  AGAAG C
C2    589                -                                      AG
C3    36                                      -ACCNN            G

A2    449  CAATCAGTGTCGTCGCGGTCGCGGTTCTAAAGT CCGCACG
A3    164                  T           C
Ax    159      G C  C       C              C
A24   161      A              T
B27   442  CAATCAGTGTCGCCGGGGTCCCAGTTCTAAAGT CCCCACG
B58   12
C1    635  CAATCAGCGTCTCCGCAGTCCCGGTTCTAAAGTCCC CAGT
C2    637         C
C3    87   GG                G
```

TABLE I-continued

Class I Seq

| | | | | | |
|---|---|---|---|---|---|
| A2 | 489 | CACCCACCGGGACTCAGA TTCTCCCCAGACGCCGAGGATGGC | | | C |
| A3 | 204 | | | TCGTGGAGACCAGGC | |
| Ax | 199 | | T | | G |
| A24 | 201 | | | | |
| B27 | 482 | CACCCACCCGGACTCAGA ATCTCCTCAGACGCCGAG ATGCG | | | G |
| B58 | 52 | | | | |
| C1 | 675 | CACCCACCCGGACTCAGA TTCTCCCCAGACGCCGAG ATGCG | | | G |
| C2 | 677 | G | | | |
| C3 | 127 | | | | |

1st EXON

| | | | | | | |
|---|---|---|---|---|---|---|
| A2 | 532 | GTCATGGCGCCCCGAACCCTCGTCCTGCTACTCTCGGGGGCTC | | | | |
| A3 | 262 | | C | | | C |
| Ax | 242 | C | C | G | A | C |
| A24 | 244 | G | | | | C |
| B27 | 524 | GTCACGGCGCCCCGAACCCTCCTCCTGCTGCTCTGGGGGGCAG | | | | |
| B58 | 94 | | G | | | |
| C1 | 717 | GTCATGGCGCCCCGAACCCTCATCCTGCTGCTCTCGGGAGCCC | | | | |
| C2 | 719 | | | | | |
| C3 | 169 | | G | | | |

| | | |
|---|---|---|
| A2 | 574 | TGGCCCTGACCCAGACCTGGGCGG |
| A3 | 305 | |
| Ax | 285 | C |
| A24 | 287 | A |
| B27 | 567 | TGGCCCTGACCGAGACCTGGGCTG |
| B58 | 137 | C |
| C1 | 760 | TGGCCCTGACCGAGACCTGGGCCT |
| C2 | 762 | |
| C3 | 212 | G |

IVS1

| | | | | | | | |
|---|---|---|---|---|---|---|---|
| A2 | 599 | GTGAGTGCGGGGTCGGG | AGGGAAACG | GCC | TCTGT | GGGGAGAAGCAACGGGCC | G |
| A3 | 329 | | C AC | | C | | G T |
| Ax | 309 | A T C | T-G -- | --- - | | G NG G | G |
| A24 | 311 | | TCG C | | C | G | CG |
| B27 | 591 | GTGAGTGCGGGGTCAGGCAGGGAAATG | | GCC | TCTGT | GGGGAGGAGCGAGGGGA | CG |
| B58 | 161 | G - | | | | | C |
| C1 | 784 | GTGAGTGCGGGGTTGGG | AGGGAAACG | GCC | TCT | GCGGAGAGGAACGAGGTGCCCG | |
| C2 | 786 | | | | | G | G |
| C3 | 236 | | T | | T | G | G |

| | | | | | | |
|---|---|---|---|---|---|---|
| A2 | 652 | CCTGGC GGGGGCGCAGGACCCGGGAAGCCGCGCCGGGAGGAGGGTCGGGCGGGTCTCAG | | | | | |
| A3 | 383 | | G | G | | C | |
| Ax | 357 | C G T | A | G | A | | |
| A24 | 367 | | A | | | | |
| B27 | 645 | CAGGC GGGGGCGCAGGACCCGGGGAGCCGCGCCGGGAGGAGGGTCGGGCGGGTCTCAG | | | | | |
| B58 | 215 | T A | | | | | |
| C1 | 838 | CCCGGC AGG CGCAGGACCCGGGGAGCCGCGCAGGGAGGAGGGTCGGGCGGGTCTCAG | | | | | |
| C2 | 840 | G | G - | | AGC | | |
| C3 | 291 | GGA | G | | | | |

| | | | |
|---|---|---|---|
| A2 | 711 | CCACTCCTCGTCCCCAG | |
| A3 | 442 | G | -C |
| Ax | 417 | TC | CT |
| A24 | 426 | | |
| B27 | 703 | CCCCTCCTCGCCCCCAG | |
| B58 | 273 | | |
| C1 | 895 | CCCCTCCTCGCCCCCAG | |
| C2 | 898 | T | |
| C3 | 351 | - | |

IVS3

| | | | | |
|---|---|---|---|---|
| A2 | 1515 | GTACCAGGGGCCACGGGGCGCCTCCCTGATCGCCTGTAGATCTCCCGGGCTGGCCTCCC | | |
| A3 | 1245 | - | | |
| Ax | 1222 | C ACA | - | |
| A24 | 1228 | | | G |
| B27 | 1508 | GTACCAGGGGCAGTGGGGAGCCTTCCCCATCTCCTATAGGTCGCCGGGGATGGCCTCCC | | |
| B58 | 1082 | | | |
| C1 | 1704 | GTACCAGGGGCAGTGGGGAGCCTTCCCCATCTCCCGTAGATCTCCCGGCATGGCCTCCC | | |
| C2 | 1705 | | T | G |
| C3 | 1155 | - | T | G |

TABLE I-continued

Class I Seq

```
A2   1574   ACAAGGAGGGGAGACAATTGGGACCAACACTAGAATATCGCCCTCCCTCTGGT
A3   1303                 C           C        G    A   T  T
Ax   1280        A A        A             T
A24  1287   C
B27  1567   ACGAGAAGAGGAGGAAAATGGGATCAGCGCTAGAATGTCGCCCTCCCTTGAAT
B58  1141
C1   1763   ACGAGGAGGGGAGGAAAATGGGATCAGCGCTAGAATATCGCCCTCCCTGAAAT
C2   1764
C3   1213

A2   1627   CCTGAGGGAGAGGAATCCTCCTGGGTTTCCAGATCCTGTACCAGAGAGTGA
A3   1356   T              T  T  T      -   GA    G
Ax   1333   T                    T             ----------
A24  1341   T
B27  1620   GGAGAATGGCATGAGTTTTCCTGAGTTTC
B58  1194
C1   1816   GGAGAATGGGATGAGTTTTCCTGAGTTTC
C2   1817
C3   1266

A2   1678   CTCTGAGGTTCCGCCCTGCTCTCTGA CACAATTAAGGGATAAAATCTCTGAAGGA
A3   1406            T  G        A A -G                  -
Ax   1372            G  -                           G    G  -
A24  1392                                                      C
B27  1649   CTCTGAGGGCCCCCTCTTCTCTCT AGGACAATTAAGGGATGACGTCTCTGAGGAA
B58  1223
C1   1845   CTCTGAGGGCCCCCTCTGCTCTCT AGGACAATTAAGGGATGAAGTCCTTGAGGAA
C2   1846
C3   1295                                    G                  A

A2   1733   ATGACGGG AAGACGATCCCTCGAATACTGATGAGTGGTTCCCTTTGACAC
A3   1460   G             T  TG T   G                        G
Ax   1426      ATGAA  G    A     G
A24  1447             A                    C
B27  1704   ATGGAGGGGAAGACAGTCCCTAGAATACTGATCAGGGGTCCCCTTTGACCC
B58  1278
C1   1900   ATGGAGGGGAAGACAGTCCCTGGAATACTGATCAGGGGTCCCCTTTGACCA
C2   1901
C3   1351                      A

A2   1783       ACACAGGCAGCAGCCTTGGG CCCG    TGACTTTTCCTCTCAGGCCTTGTTCTCTGC
A3   1510       ----C        GA  G
Ax   1477       ----T              C
A24  1497       ----C              A
B27  1755       CTGCAGCAGCCTTGGGAACCG    TGACTTTTCCTCTCAGGCCTTGTTCACAGC
B58  1329                                                              T T
C1   1951   CTTTGACCACTGCAGCAGCTGTGGTCAGGCTGCTGACCTTT CTCTCAGGCCTTGTTCTCTGC
C2   1952
C3   1411   ---------

A2   1837   TTCACACTCAATGTGTGTGGGGGTCTGAGTCCAGCACTTCTGAGTCCTTCAGCC
A3   1560                                                        C
Ax   1528                   C             ----------------C
A24  1547                                                        C
B27  1806   CTCACACTCAGTGTGTTTGGGGCTCTGATTCCAGCACTTCTGAGTCACTTTACC
B58  1380
C1   2013   CTCACGTTCAATGTGTTTGAAGGTTTGATTCCAGCTTTTCTGAGTCCTTCGGCC
C2   2014
C3   1464       C

A2   1891   TCCACTCAGGTCAGGACCAGAAGTCGCTGTTCCCTCTTCAGGGACTAGAA TTTCCACGGAATAG
A3   1614                                   TC        A           --------------
Ax   1567                                                          T
A24  1600                                             A           --------------
B27  1860   TCCACTCAGATCAGGAGCAGAAGTCCCTGTTCCCCGCTCAGAGACT CGAACTTTCCAATGAATAG
B58  1434
C1   2067   TCCACTCAGGTCAGGACCAGAAGTCGCTGTTCCTCCCTCAGAGACTAGAACTTTCCAATGAATAG
C2   2068
C3   1518
```

TABLE I-continued

Class I Seq

```
A2   1955  GAGATTATCCCAGGTGCCTGTGTCCAGGCTGGTGTCTGGGTTCTGTGCTCCCTTCCCCA
A3   1664  --
Ax   1632           T T        C    T         T
A24  1650  --                A                           A  T       G
B27  1925  GAGATTATCCCAGGTGCCTGCGTCCAGGCTGGTGTCTGGGTTCTGTGCCC CTTCCCCA
B58  1499                                                      —
C1   2132  GAGATTATCCCAGGTGCCTGTGTCCAGGCTGGCGTCTGGGTTCTGTGCCCCCTTCCCCA
C2   2133
C3   1583

A2   2014  TCCCAGGTGTCCTGTCCATTCTCAAGA TAGCCACATGTGTGCTGGAGGAGTGTCCCATG
A3   1721           G                      G      C         T
Ax   1691  C T   CA       A              G      C         T
A24  1706                                 G      CA        T
B27  1983  CCCCAGGTGTCCTGTCCATTCTC AGGCTGGTCACATGGGTGGTCCTAGGGTGTCCCATG
B58  1557  A
C1   2191  CCCCAGGTGTCCTGTCCATTCTC AGGATGGTCACATGGGCGCTGTTGGAGTGTCGCAAG
C2   2192                                  A
C3   1642           G

A2   2073  ACAGATCGAAAATGCCTGAATGATCTGACTCT   TCCTGACAG  2113
A3   1780          GC           TT                C T        1820
Ax   1750          GC           TT         TT     C T        1791
A24  1765       G GCAAAA-------------------- -    C T        1784
B27  2042  AGAGATGCAAAGCGCCTGAATTTTCTGACTCTTCCCAT   CAG  2083
B58  1616                                                    1656
C1   2250  AGAGATACAAAGTGTCTGAATTTTCTGACTCTTCCCGT   CAG  2290
C2   2251                                       G            2292
C3   1701                                                    1741
```

TABLE 2

DQA1 Seq

```
A3   1    GATCTCTGTGTAGAATGTCCTGTTCTGAGCCAGTCCTGAGAGGAAAGGAAGTATAATCAA
A1.2 1                    G      A
A4.1 1              C     G                                 A   A C     G

A3   61   TTTGTTATTAACTGATGAAAGAATTAAGTGAAAGATAAACCTTAGGAAGC AGAGGGAAGT
A1.2 61             CA                              T C           C
A4.1 61                                             G T           C   A

A3   121  TAA    TCTATGACTAAGAAAGTTAAGTACTCTGATAACTCATTCATTCCTTCT
A1.2 122  A  CCTAA T C          C   A   A
A4.1 122  A  CCTAA   C          C   A   CA  A

A3   172  TTTGTTCATTTACATT ATTTAATCACAAGTCTATGATGTGCCAGGCTCTCAGGAAATA
A1.2 178          A                T   C   C              A
A4.1 178          A         G      T   CG                 A

A3   230  GTGAAAATTGG CACGCGATATTCTGCCCTTGTGTAGCACACACCGTAGTGGGAAAG
A1.2 236      A       A    T                       G        TAG
A4.1 237      A   C   A    T T                     G        TTA

A3   286  AA GTGCACTTTTAACCGGACAACTATCAACACGAAGCGGGGAGGAAGCAGGGG
A1.2 293       A         T       C     T     A
A4.1 294       A C  A            C     AT    A T

A3   339  CTGGAAATGTCCACAGACTTTGCCAAA GACAAAGCCCATAATATCTGAAAGTCAG
A1.2 347                  G         AA TG         T
A4.1 348  T               G G         TG       G  T

A3   394  TTTCTTC  CATCATTTTGTGTATTAAGGTTCTTTATTCCCCTGTTCTCTGCCTTCCT
A1.2 403  G CT                                C    T         C
A4.1 403    CT  TCAT                          G C              CA

A3   450  GCTTGTCATCTTCACTCATCAGCTGACCATGTTGCCTCTTACGGTGTAAACTTGTACCAG
A1.2 459                             C           GT
A4.1 462                             C   C       T

A3   510  TCTTATGGTCCCTCTGGGCAGTACAGCCATGAATTTGATGGAGACGAGGAGTTCTAT
A1.2 519  T C             C      C                    T C      C
A4.1 522    C             C      C                    T C      C
```

TABLE 2-continued

| DQA1 | Seq | |
|---|---|---|
| A3   | 567 | GTGGACCTGGAGAGGAAGGAGACTGTCTGGCAGTTGCCTCTGTTCCGCAGATTTA |
| A1.2 | 576 |                           C        G  G      GA    A      A        G |
| A4.1 | 579 |      G                     TGT        G TC   A ACA |
| A3   | 622 | GAAGATTTGACCCGCAATTTGCACTGACAAACATCGCTGTGCTAAAACATAACTTGA |
| A1.2 | 631 |    G T         GGG      G       G     GC      C |
| A4.1 | 634 | ---                                        C |
| A3   | 679 | ACATCGTGATTAAACGCTCCAACTCT<u>ACCGCTGCTACCAATGGT</u>ATGTGTCCACCATTCTG |
| A1.2 | 688 |     A        A                                      C |
| A4.1 | 688 |  GTC                                             A  A |
| A3   | 740 | CCTTTCTTTAC    TGATTTATCCCTTTATACCAAGTTTCATTATTTTCTTT |
| A1.2 | 749 |   C      TTAA A GC     CC        G                   C |
| A4.1 | 749 |   CC                 C                        A |
| A3   | 789 | <u>CCAAGAGGTCCCCAGATC</u>    806 |
| A1.2 | 802 |                       819 |
| A4.1 | 798 |                       815 |

TABLE 3

DQB1 Seq

```
  1  AAGCTTGTGCTCTTTCCATGAATAAATGTCTCTATCTAGGACTCAGAGGT
                    GG         T    T            A
                                              G

51  GTAGG   TCCTTTCCAACATAGAAGGGAGTGA    ACCTCAACGGG ACTTGGGA G
            TT                                      TT
        C   AC   C   TTT TA C CA AC    GTGA      CA   C
                         A    T                  AT   C       A

101  GGTAAATCTAGGCATGGGAAGGA<u>AGGTATTTTACCCAGGGACCAAGAGAA</u>
                C
                            G

151  <u>TA</u>CGCGTGTCAGAACGAGGCCAGGCTTAATTCCTGGACCTATCTCGTCAT
         G   A   G  -    A  T             G
         A               A       T        CG     A

201  TCCGTTGAACTCTCAGATTTATGTGGATAACTTTATCTCTGAGGTATCCA
             C    G  G                              C
             C       A  G          T                T

251  GGAGCTTCATGAAAAATGGGATTTCATGCGAGAACGCCCTGAT CCCTCTA
             C    G   A
             CA   G                              G        T

301  AGTGCAGAGGTGC<u>ATGTAAAATCAGCCCGACTGCCTCTTCGCTGGGTTCA</u>
                  C                              A   T
                  CT                             C   C

351  CAGGCTCAGGCAGGGACAGGGCTTTCCTCCCTTTCCTGGATGTAGGAAGG
                CG  A                        CC
                 C                 G         CC  C

401  C AGATTCCAGAAGCCCGCAAAGAAGGCGGGCAGAGCTGGGCAGAGCCGCC
         CG    C    A C CG   G         G   -  N N N
         G     C      C G    G         G

451  GGGAGGATCCCAGGTCTGGAGCGCCAGGCACGGGCGGGCGGGAACTGGAG
                        C    G                       T T
         C     A  A
```

TABLE 3-continued

DQB1 Seq

```
501   GTCGCGCGGGCGGTTCCACAGCTCCAGGCCGGGTCAGGGCGGCGGCTGCG
                T              G            T
                               G

551   GGGGCGGCCGGGCTGGGGCC            TGACTGACCGGCCGGTGATTCCCCGCAGAG
              A       -       GCA     ---
                              GGGCCGGGGCC

601   GATTTCGTGTACCAGTTTAAGGGCATGTGCTACTTCACCAACGGGACGGA
                                                            A

651   GCGCGTGCGTCTTGTAACCAGACACATCTATAACCGAGAGGAGTACGCGC
                G G      AG               A    AT  T
                G        T                         A

701   GCTTCGACAGCGACGTGGGGGTGTACCGGGCGGTGACGCCGCAGGGGCGG
                         A T          T T    T
                           T                 C

751   CCTGTTGCCGAGTACTGGAACAGCCAGAAGGAAGTCCTGGAGAGGACCCG
            CC                  CA         AA
            CC

801   GGCGGAGTTGGA CACGGTGTGCAGACACAACTACGAGGTGGGGTACCGCG
              C G       G              C T   A CT      A
                    A                  C T   A CT      A

851   GGATCCTGCAGAGGAGAGGTGAGCTTCGTCGCCCCTCCGTGAGCGC ACCC
                          G
      C C T     C C         GG       -T T C   GC C
      C C T     C C         G        G         GC C T

901   TTGGCCGGGACCCCGAGTCTCTGTGCCGGGAGGGCG ATGGGGGCGAGGTC
            ------ A      C  A      G  CAA   T T  C
            A    G  A     CCG          GCGAA    C  C

951   TCTGAAATCTTGAGCCCAGTTCATTCCACCCCAGGGAAAGGAGGCGGCGG
            -C -       C  GG
         G  C         TT           - CTG C-   A  A

1001  CGGGGGTGGTGGGGGCAGGTGCATCGGAGGGGCGGGGACCTAGGGCAGAG
      CGGT   -   C     T              A

1051  CAGGGGGACAAGCAGAGTTGGCCAGGCTGCCTAGTGTCCCCCCCAGCCTC
              G       T A         T G    - T

1101  CTCGTCCGTCGGCCTCGTCCTCTGCTCTGGACGTTTCTCGCCTCGTGCCT
         C
         C             C          C      -  T

1151  TATGCGTTTGCCTCCTCGTGCCTTACCTTCGCTAAGCAGTTCTCTCTGCC
                                  TA

1201  CCCAGTGCCCACCCTCTTCCCCTGCCCGCCGGCCTCGCTAGCACTGCCCC
           A TT G              C   CG              G

1251  ACCCAGCAAGGCCCACAGTCGCGCATTCGCCGCA GGAAGCTT         1292
                    T CG
          G      T      CTA A AGC CATG AGTGGGAAGCTT
```

TABLE 4

DPB1 Seq

| | | | | | |
|---|---|---|---|---|---|
| DPB4.1 | 7546 | | | | GGGAAGATTTGGGAAGAATCGTTAATAT |
| DPB4.1 | 7574 | TGAGAGAGAGAGGGAGAAAGAGGATTAGAT<u>GAGAGTGGCGCCTCCGCTCATGTCCGCCCC</u> | | | |
| DPB4.1 | 7634 | CTCCCCGCAGAGAATTACCTTTTCCAGGGACGGCAGGAATGCTACGCGTTTAATGGGACA | | | |
| DPB9 | | GGAT        G  GCA    TT | | | |
| New DPw3 | | GGAT        G  GCA    TT | | | |
| BPB4.1 | 7694 | CAGCGCTTCCTGGAGAGATACATCTACAACCGGGAGGAGTTCGCGCGCTTCGACAGCGAC | | | |
| DPB9 | |                                           T | | | |
| New DPw3 | |                                           T | | | |
| DPB4.1 | 7754 | GTGGGGGAGTTCCGGGCGGTGACGGAGCTGGGGCGGCCTGCTGCGGAGTACTGGAACAGC | | | |
| DPB9 | |                                  A  A     C | | | |
| New DPw3 | |                                  A  A     C | | | |
| DPB4.1 | 7814 | CAGAAGGACATCCTGGAGGAGAAGCGGGCAGTGCCGGACAGGATGTGCAGACACAACTAC | | | |
| DPB9 | |                    G                          G A | | | |
| New | |      C                                            G A | | | |
| DPw3 | |      C                                            G A | | | |
| DPB4.1 | 7874 | GAGCTGGGCGGGCCCATGACCCTGCAGCGCCGAGGT<u>GAGTGAGGGCTTTGGGCCGGCGGT</u> | | | |
| DPB9 | |      A  A G   G | | | |
| New | |      A  A G   G | | | |
| DPw3 | |      A  A G   G | | | |
| DPB4.1 | 7934 | CCCAGGGCAGCCCCGCGGGCCCGTGCCCAG | | | |

Primers for HLA Loci

Exemplary HLA locus-specific primers are listed below. Each of the primers hybridizes with at least about 15 consecutive nucleotides of the designated region of the allele sequence. The designation of an exemplary preferred primer together with its sequence is also shown. For many of the primers, the sequence is not identical for all of the other alleles of the locus. For each of the following preferred primers, additional preferred primers have sequences which correspond to the sequences of the homologous region of other alleles of the locus or to their complements.

In one embodiment, Class I loci are amplified by using an A, B or C locus-specific primer together with a Class I locus-specific primer. The Class I primer preferably hybridizes with IVS III sequences (or their complements) or, more preferably, with IVS I sequences (or their complements). The term "Class I-specific primer", as used herein, means that the primer hybridizes with an allele sequence (or its complement) for at least two different Class I loci and does not hybridize with Class II locus allele sequences under the conditions used. Preferably, the Class I primer hybridizes with at least one allele of each of the A, B and C loci. More preferably, the Class I primer hybridizes with a plurality of, most preferably all of, the Class I allele loci or their complements. Exemplary Class I locus-specific primers are also listed below.

HLA Primers

A Locus-Specific Primers
allelic location: nt 1735-1757 of A3
designation: SGD009.AIVS3.R2NP
sequence: CATGTGGCCATCTTGAGAATGGA
allelic location: nt 1541-1564 of A2
designation: SGD006.AIVS3.R1NP
sequence: GCCCGGGAGATCTACAGGCGATCA
allelic location: nt 1533-1553 of A2
designation: A2.1
sequence: CGCCTCCCTGATCGCCTGTAG
allelic location: nt 1667-1685 of A2
designation: A2.2
sequence: CCAGAGAGTGACTCTGAGG
allelic location: nt 1704-1717 of A2
designation: A2.3
sequence: CACAATTAAGGGAT B Locus-Specific Primers
allelic location: nt 1108-1131 of B17
designation: SGD007.BIVS3.R1NP
sequence: TCCCCGGCGACCTATAGGAGATGG
allelic location: nt 1582-1604 of B17
designation: SGD010.BIVS3.R2NP
sequence: CTAGGACCACCCATGTGACCAGC
allelic location: nt 500-528 of B27
designation: B2.1
sequence: ATCTCCTCAGACGCCGAGATGCGTCAC
allelic location: nt 545-566 of B27
designation: B2.2
sequence: CTCCTGCTGCTCTGGGGGGCAG
allelic location: nt 1852-1876 of B27
designation: B2.3
sequence: ACTTTACCTCCACTCAGATCAGGAG
allelic location: nt 1945-1976 of B27
designation: B2.4
sequence: CGTCCAGGCTGGTGTCTGGGTTCTGTGCCCCT
allelic location: nt 2009-2031 of B27
designation: B2.5
sequence: CTGGTCACATGGGTGGTCCTAGG
allelic location: nt 2054-2079 of B27
designation: B2.6
sequence: CGCCTGAATTTTCTGACTCTTCCCAT C Locus-Specific Primers
allelic location: nt 1182-1204 of C3
designation: SGD008.CIVS3.R1NP
sequence: ATCCCGGGAGATCTACAGGAGATG
allelic location: nt 1665-1687 of C3
designation: SGD011.CIVS3.R2NP
sequence: AACAGCGCCCATGTGACCATCCT
allelic location: nt 499-525 of C1
designation: C2.1
sequence: CTGGGGAGGCGCCGCGTTGAGGATTCT
allelic location: nt 642-674 of C1
designation: C2.2
sequence: CGTCTCCGCAGTCCCGGTTCTAAAGTTC-CCAGT
allelic location: nt 738-755 of C1
designation: C2.3
sequence: ATCCTCGTGCTCTCGGGA
allelic location: nt 1970-1987 of C1
designation: C2.4
sequence: TGTGGTCAGGCTGCTGAC
allelic location: nt 2032-2051 of C1
designation: C2.5
sequence: AAGGTTTGATTCCAGCTT
allelic location: nt 2180-2217 of C1
designation: C2.6
sequence: CCCCTTCCCCACCCCAGGTGTTCCTGTC-CATTCTTCAGGA
allelic location: nt 2222-2245 of C1
designation: C2.7
sequence: CACATGGGCGCTGTTGGAGTGTCG
Class I Loci-Specific Primers
allelic location: nt 599-620 of A2
designation: SGD005.IIVS1.LNP
sequence: GTGAGTGCGGGGTCGGGAGGGA
allelic location: nt 489-506 of A2
designation: 1.1
sequence: CACCCACCGGGACTCAGA
allelic location: nt 574-595 of A2
designation: 1.2
sequence: TGGCCCTGACCCAGACCTGGGC
allelic location: nt 691-711 of A2
designation: 1.3
sequence: GAGGGTCGGGCGGGTCTCAGC
allelic location: nt 1816-1831 of A2
designation: 1.4
sequence: CTCTCAGGCCTTGTTC
allelic location: nt 1980-1923 of A2
designation: 1.5
sequence: CAGAAGTCGCTGTTCC
DQA1 Locus-Specific Primers
allelic location: nt 23-41 of DQA3
designation: SGD001.DQA1.LNP
sequence: TTCTGAGCCAGTCCTGAGA
allelic location: nt 45-64 of DQA3
designation: DQA3 E1a
sequence: TTGCCCTGACCACCGTGATG
allelic location: nt 444-463 of DQA3
designation: DQA3 E1b
sequence: CTTCCTGCTTGTCATCTTCA
allelic location: nt 536-553 of DQA3
designation: DQA3 E1c
sequence: CCATGAATTTGATGGAGA
allelic location: nt 705-723 of DQA3
designation: DQA3 E1d
sequence: ACCGCTGCTACCAATGGTA
allelic location: nt 789-806 of DQA3
designation: SGD003.DQA1.RNP
sequence: CCAAGAGGTCCCCAGATC
DRA Locus-Specific Primers
allelic location: nt 49-68 of DRA HUMMHDRAM (1183 nt sequence, Accession No. K01171)
designation: DRA E1
sequence: TCATCATAGCTGTGCTGATG
allelic location: nt 98-118 of DRA HUMMHDRAM (1183 nt sequence, Accession No. K01171)
designation: DRA 5'E2 (5' indicates the primer is used as the 5' primer)
sequence: AGAACATGTGATCATCCAGGC
allelic location: nt 319-341 of DRA HUMMHDRAM (1183 nt sequence, Accession No. K0117 1)
designation: DRA 3'E2
sequence: CCAACTATACTCCGATCACCAAT
DRB Locus-Specific Primers
allelic location: nt 79-101 of DRB HUMMHDRC (1153 nt sequence, Accession No. K01171)
designation: DRB E1
sequence: TGACAGTGACACTGATGGTGCTG
allelic location: nt 123-143 of DRB HUMMHDRC (1153 nt sequence, Accession No. K01171)
designation: DRB 5'E2
sequence: GGGGACACCCGACCACGTTTC
allelic location: nt 357-378 of DRB HUMMHDRC (1153 nt sequence, Accession No. K01171)
designation: DRB 3'E2
sequence: TGCAGACACAACTACGGGGTTG
DOB1 Locus-Specific Primers
allelic location: nt 509-532 DQB1 DQw1,a
designation: DQB E1
sequence: TGGCTGAGGGCAGAGACTCTCCC
allelic location: nt 628-647 of DQB1 DQw1,a
designation: DQB 5'E2
sequence: TGCTACTTCACCAACGGGAC
allelic location: nt 816-834 of DQB1 DQw1,a
designation: DQB 3'E2
sequence: GGTGTGCACACACAACTAC
allelic location: nt 124-152 of DQB1 DQw1,a
designation: DQB 5'IVS1a
sequence: AGGTATTTTACCCAGGGACCAAGAGAT
allelic location: nt 314-340 of DQB1 DQw1,a
designation: DQB 5'IVS1b
sequence: ATGTAAAATCAGCCCGACTGCCTCTTC
allelic location: nt 1140-1166 of DQB1 DQw1,a
designation: DQB 3'IVS2
sequence: GCCTCGTGCCTTATGCGTTTGCCTCCT
DPB1 Locus-Specific Primers
allelic location: nt 6116-6136 of DPB1 4.1
designation: DPB E1
sequence: TGAGGTTAATAAACTGGAGAA
allelic location: nt 7604-7624 of DPB1 4.1
designation: DPB 5'IVS1
sequence: GAGAGTGGCGCCTCCGCTCAT
allelic location: nt 7910-7929 of DPB1 4.1
designation: DPB 3'IVS2
sequence: GAGTGAGGGCTTTGGGCCGG
Primer Pairs for HLA Analyses It is well understood that for each primer pair, the 5' upstream primer hybridizes with the 5' end of the sequence to be amplified and the 3' downstream primer hybridizes with the complement of the 3' end of the sequence. The primers amplify a sequence between the regions of the DNA to which the primers bind and its complementary sequence including the regions to which the primers bind. Therefore, for each of the primers described above, whether the primer binds to the HLA-encoding strand or its complement depends on whether the primer functions as the 5' upstream primer or the 3' downstream primer for that particular primer pair.

In one embodiment, a Class I locus-specific primer pair includes a Class I locus-specific primer and an A, B or C locus-specific primer. Preferably, the Class I locus-specific primer is the 5' upstream primer and hybridizes with a portion of the complement of IVS I. In that case, the locus-specific primer is preferably the 3' downstream primer and hybridizes with IVS III. The primer pairs amplify a sequence of about 1.0 to about 1.5 Kb.

In another embodiment, the primer pair comprises two locus-specific primers that amplify a DNA sequence that does not include the variable exon(s). In one example of that embodiment, the 3' downstream primer and the 5' upstream primer are Class I locus-specific primers that hybridize with IVS III and its complement, respectively. In that case a sequence of about 0.5 Kb corresponding to the intron sequence is amplified.

Preferably, locus-specific primers for the particular locus, rather than for the HLA class, are used for each primer of the primer pair. Due to differences in the Class II gene sequences, locus-specific primers which are specific for only one locus participate in amplifying the DRB, DQA1, DQB and DPB loci. Therefore, for each of the preferred Class II locus primer pairs, each primer of the pair participates in amplifying only the designated locus and no other Class II loci.

Analytical Methods

In one embodiment, the amplified sequence includes sufficient intron sequences to encompass length polymorphisms. The primer-defined length polymorphisms (PDLPS) are indicative of the HLA locus allele in the sample. For some HLA loci, use of a single primer pair produces primer-defined length polymorphisms that distinguish between some of the alleles of the locus. For other loci, two or more pairs of primers are used in separate amplifications to distinguish the alleles. For other loci, the amplified DNA sequence is cleaved with one or more restriction endonucleases to distinguish the alleles. The primer-defined length polymorphisms are particularly useful in screening processes.

In anther embodiment, the invention provides an improved method that uses PCR amplification of a genomic HLA DNA sequence of one HLA locus. Following amplification, the amplified DNA sequence is combined with at least one endonuclease to produce a digest. The endonuclease cleaves the amplified DNA sequence to yield a set of fragments having distinctive fragment lengths. Usually the amplified sequence is divided, and two or more endonuclease digests are produced. The digests can be used, either separately or combined, to produce RFLP patterns that can distinguish between individuals. Additional digests can be prepared to provide enhanced specificity to distinguish between even closely related individuals with the same HLA type.

In a preferred embodiment, the presence of a particular allele can be verified by performing a two step amplification procedure in which an amplified sequence produced by a first primer pair is amplified by a second primer pair which binds to and defines a sequence within the first amplified sequence. The first primer pair can be specific for one or more alleles of the HLA locus. The second primer pair is preferably specific for one allele of the HLA locus, rather than a plurality of alleles. The presence of an amplified sequence indicates the presence of the allele, which is confirmed by production of characteristic RFLP patterns.

To analyze RFLP patterns, fragments in the digest are separated by size and then visualized. In the case of typing for a particular HLA locus, the analysis is directed to detecting the two DNA allele sequences that uniquely characterize that locus in each individual. Usually this is performed by comparing the sample digest RFLP patterns to a pattern produced by a control sample of known HLA allele type. However, when the method is used for paternity testing or forensics, the analysis need not involve identifying a particular locus or loci but can be done by comparing single or multiple RFLP patterns of one individual with that of another individual using the same restriction endonuclease and primers to determine similarities and differences between the patterns.

The number of digests that need to be prepared for any particular analysis will depend on the desired information and the particular sample to be analyzed. For example, one digest may be sufficient to determine that an individual cannot be the person whose blood was found at a crime scene. In general, the use of two to three digests for each of two to three HLA loci will be sufficient for matching applications (forensics, paternity). For complete HLA haplotyping; e.g., for transplantation, additional loci may need to be analyzed.

As described previously, combinations of primer pairs can be used in the amplification method to amplify a particular HLA DNA locus irrespective of the allele present in the sample. In a preferred embodiment, samples of HLA DNA are divided into aliquots containing similar amounts of DNA per aliquot and are amplified with primer pairs (or combinations of primer pairs) to produce amplified DNA sequences for additional HLA loci. Each amplification mixture contains only primer pairs for one HLA locus. The amplified sequences are preferably processed concurrently, so that a number of digest RFLP fragment patterns can be produced from one sample. In this way, the HLA type for a number of alleles can be determined simultaneously.

Alternatively, preparation of a number of RFLP fragment patterns provides additional comparisons of patterns to distinguish samples for forensic and paternity analyses where analysis of one locus frequently fails to provide sufficient information for the determination when the sample DNA has the same allele as the DNA to which it is compared.

The use of HLA types in paternity tests or transplantation testing and in disease diagnosis and prognosis is described in Basic & Clinical Immunology, 3rd Ed (1980) Lange Medical Publications, pp 187–190, which is incorporated herein by reference in its entirety. HLA determinations fall into two general categories. The first involves matching of DNA from an individual and a sample. This category involves forensic determinations and paternity testing. For category 1 analysis, the particular HLA type is not as important as whether the DNA from the individuals is related. The second category is in tissue typing such as for use in transplantation. In this case, rejection of the donated blood or tissue will depend on whether the recipient and the donor express the same or different antigens. This is in contrast to first category analyses where differences in the HLA DNA in either the introns or exons is determinative.

For forensic applications, analysis of the sample DNA of the suspected perpetrator of the crime and DNA found at the crime scene are analyzed concurrently and compared to determine whether the DNA is from the same individual. The determination preferably includes analysis of at least three digests of amplified DNA of the DQA1 locus and preferably also of the A locus. More preferably, the determination also includes analysis of at least three digests of amplified DNA of an additional locus, e.g. the DPB locus. In this way, the probability that differences between the DNA samples can be discriminated is sufficient.

For paternity testing, the analysis involves comparison of DNA of the child, the mother and the putative father to determine the probability that the child inherited the obligate haplotype DNA from the putative father. That is, any DNA sequence in the child that is not present in the mother's DNA must be consistent with being provided by the putative father. Analysis of two to three digests for the DQA1 and preferably also for the A locus is usually sufficient. More preferably, the determination also includes analysis of digests of an additional locus, e.g. the DPB locus.

For tissue typing determinations for transplantation matching, analysis of three loci (HLA A, B, and DR) is often sufficient. Preferably, the final analysis involves comparison of additional loci including DQ and DP.

Production of RFLP Fragment Patterns

The following table of exemplary fragment pattern lengths demonstrates distinctive patterns. For example, as shown in the table, BsrI cleaves A2, A3 and A9 allele amplified sequences defined by primers SGD005.IIVS1.LNP and SGD009.AIVS3.R2NP into sets of fragments with the following numbers of nucleotides (740, 691), (809, 335, 283) and (619, 462, 256, 93), respectively. The fragment patterns clearly indicate which of the three A alleles is present. The following table illustrates a number of exemplary endonucleases that produce distinctive RFLP fragment patterns for exemplary A allele sequences.

Table 2 illustrates the set of RFLP fragments produced by use of the designated endonucleases for analysis of three A locus alleles. For each endonuclease, the number of nucleotides of each of the fragments in a set produced by the endonuclease is listed. The first portion of the table illustrates RFLP fragment lengths using the primers designated SGD009.AIVS3.R2NP and SGD005.IIVS1.LNP which produce the longer of the two exemplary sequences. The second portion of the table illustrates RFLP fragment lengths using the primers designated SGD006.AIVS3.R1NP and SGD005.IIVS1.LNP which produce the shorter of the sequences. The third portion of the table illustrates the lengths of fragments of a DQA1 locus-specific amplified sequence defined by the primers designated SGD001.DQA1.LNP and SGD003.DQA1.RNP.

As shown in the Table, each of the endonucleases produces a characteristic RFLP fragment pattern which can readily distinguish which of the three A alleles is present in a sample.

TABLE 5

RFLP FRAGMENT PATTERNS

A - Long

| | | | | | | | | | | |
|---|---|---|---|---|---|---|---|---|---|---|
| BsrI | A2 | | 740 | 691 | | | | | | |
| | A3 | 809 | | | | | 335 | 283 | | |
| | A9 | | | | 619 | 462 | | | 256 | 93 |
| Cfr101 | A2 | 1055 | | | 399 | 245 | | | | |
| | A3 | | | 473 | 399 | 247 | | | | |
| | A9 | | 786 | | 399 | | | | | |
| DraII | A2 | 698 | | | | | 251 | 138 | | |
| | A3 | | | | 369 | 315 | 251 | 247 | | |
| | A9 | | 596 | 427 | | | 251 | | | 80 |
| FokI | A2 | | 728 | | 248 | | | 151 | | |
| | A3 | | | 515 | | 225 | 213 | 151 | | |
| | A9 | 1004 | | | | | | 151 | | |
| GsuI | A2 | | 868 | | 547 | | | | 36 | |
| | A3 | 904 | | | | 523 | | | | |
| | A9 | | | 638 | | | 419 | 373 | | |
| HphI | A2 | 1040 | | | | | 239 | | | 72 |
| | A3 | | | 419 | 375 | | | 218 | 163 | |
| | A9 | | 643 | 419 | 373 | | | | | |
| MboII | A2 | | 1011 | | | 165 | 143 | 132 | | |
| | A3 | | | 893 | 194 | | 143 | | 115 | |
| | A9 | 1349 | | | | | | | | 51 |
| PpumI | A2 | 698 | | | | | 295 | 251 | | 138 |
| | A3 | | | | 369 | 364 | | 251 | 242 | |
| | A9 | | 676 | 503 | | | | 251 | | |
| PssI | A2 | 695 | | | | | 295 | 251 | | 138 |
| | A3 | | | | 366 | 315 | | 251 | 242 | |
| | A9 | | 596 | 427 | | | | 251 | | |

A - Short

| | | | | | | | | | | |
|---|---|---|---|---|---|---|---|---|---|---|
| BsrI | A2 | 691 | | | | 254 | | | | |
| | A3 | | | 345 | 335 | 283 | | | | |
| | A9 | | 619 | | | | 256 | 93 | | |
| Cfr101 | A2 | | | | | | | | | |
| | A3 | | | | | | | | | |
| | A9 | | | | | | | | | |
| DraII | A2 | | | 295 | 251 | 210 | 138 | | | |
| | A3 | | 315 | | 251 | 210 | | | | |
| | A9 | 427 | | | 251 | 210 | | | | |
| FokI | A2 | | 293 | 248 | | | 151 | 143 | 129 | 51 |
| | A3 | | | | 225 | 213 | 151 | 143 | 129 | 51 |
| | A9 | 539 | | | | | 151 | 146 | 129 | |
| GsuI | A2 | | 868 | | | 61 | 36 | | | |
| | A3 | 904 | | | | 59 | | | | |

TABLE 5-continued

RFLP FRAGMENT PATTERNS

|      |       |     |     |     |     |     |     |     |    |
|------|-------|-----|-----|-----|-----|-----|-----|-----|-----|
|      | A9    |     |     | 414 | 373 | 178 |     |     |    |
| HphI | A2    | 554 |     |     | 339 |     |     |     |    |
|      | A3    |     | 411 | 375 |     | 177 |     |     |    |
|      | A9    |     |     | 414 | 373 |     | 178 |     |    |
| MboII| A2    |     |     |     |     |     |     |     |    |
|      | A3    |     |     |     |     |     |     |     |    |
|      | A9    |     |     |     |     |     |     |     |    |
| PpumI| A2    |     |     | 295 | 257 |     | 212 |     | 69 |
|      | A3    |     | 364 |     |     | 251 | 210 | 72  | 66 |
|      | A9    | 503 |     |     |     | 251 | 211 |     |    |
| PssI | A2    |     |     | 295 | 251 | 219 |     | 72  |    |
|      | A3    |     | 315 |     | 251 |     | 297 | 72  | 66 |
|      | A9    | 427 |     |     | 251 |     | 208 | 72  |    |

DQA1

AluI

| | | | | | | | | | | | | | | | | | |
|---|---|---|---|---|---|---|---|---|---|---|---|---|---|---|---|---|---|
| DQA3   | 449 |     | 335 |     |     |     |     | 122 |     |     |     |     |     |     |    |    |   |
| DQA4.1 |     | 338 | 332 |     |     |     |     |     |     |     |     |     |     |     |    |    |   |
| DQA1.2 |     |     | 335 | 287 |     |     |     | 123 |     |     |     |     | 52  |     |    |    |   |

CviJI

| | | | | | | | | | | | | | | | | | |
|---|---|---|---|---|---|---|---|---|---|---|---|---|---|---|---|---|---|
| DQA3   |     |     |     |     | 271 |     | 187 | 122 |     | 99 |    | 64 | 34 |    | 7 |
| DQA4.1 |     |     |     |     | 277 | 219 |     |     | 102 |    | 79 |    | 55 | 36 | 17 | 7 |
| DQA1.2 |     |     |     |     |     |     | 201 |     | 101 | 99 | 80 | 76 | 55 | 36 | 35 | 7 |

DdeI

| | | | | | | | | | | | | | |
|---|---|---|---|---|---|---|---|---|---|---|---|---|---|
| DQA3   | 587 |     |     |     |     |     |     | 88 | 65 |    | 30 | 11 | 3 |
| DQA4.1 |     | 388 |     |     |     | 194 |     | 89 | 64 | 36 |    | 11 | 3 |
| DQA1.2 |     | 395 |     |     |     | 165 |     | 88 | 65 | 41 | 36 | 11 | 3 |

MboII

| | | | | | | | | | | |
|---|---|---|---|---|---|---|---|---|---|---|
| DQA3   |     | 366 |     |     | 184 | 172 |     |    | 62 |    |    |
| DQA4.1 | 407 | 353 |     |     |     |     |     |    |    | 32 |    |
| DQA1.2 |     | 330 | 316 |     |     |     |     | 89 |    | 32 | 30 |

MnlI

| | | | | | | | | | | | | | | | |
|---|---|---|---|---|---|---|---|---|---|---|---|---|---|---|---|
| DQA3   |     |     |     | 214 | 176 | 172 |     |     |     | 72  | 43 | 36 | 23 | 21 | 17 | 10 |
| DQA4.1 |     |     | 294 |     |     | 179 |     |     | 149 |     | 40 | 36 | 33 | 21 |    |    |
| DQA1.2 |     |     |     | 216 |     |     |     | 136 | 123 | 73  | 54 | 44 | 40 | 36 | 24 | 21 | 15 | 10 | 5 |

NlaIII

| | | | | | | | | | | | | |
|---|---|---|---|---|---|---|---|---|---|---|---|---|
| DQA3   | 458 |     |     | 266 |     |     |     |     |     | 60 |    |    |
| DQA4.1 |     |     | 300 | 263 | 229 |     |     |     |     |    |    |    |
| DQA1.2 |     |     |     |     | 223 | 190 |     | 124 | 116 | 75 | 39 | 30 |

TthIIII

| | | | | | | | | |
|---|---|---|---|---|---|---|---|---|
| DQA3   |     | 417 |     |     | 226 |     | 141 |    |
| DQA4.1 | 426 |     | 371 |     |     |     |     |    |
| DQA1.2 | 428 |     |     |     |     | 148 | 141 | 75 |

Screening Analysis for Genetic Disease

Carriers of genetic diseases and those affected by the disease can be identified by use of the present method. Depending on the disease, the screening analysis can be used to detect the presence of one or more alleles associated with the disease or the presence of haplotypes associated with the disease. Furthermore, by analyzing haplotypes, the method can detect genetic diseases that are not associated with coding region variations but are found in regulatory or other untranslated regions of the genetic locus. The screening method is exemplified below by analysis of cystic fibrosis (CF).

Cystic fibrosis is an autosomal recessive disease, requiring the presence of a mutant gene on each chromosome. CF is the most common genetic disease in Caucasians, occurring once in 2,000 live births. It is estimated that one in forty Caucasians are carriers for the disease.

Recently a specific deletion of three adjacent basepairs in the open reading frame of the putative CF gene leading to the loss of a phenylalanine residue at position 508 of the predicted 1480 amino acid polypeptide was reported [Kerem et al. Science 245:1073–1080 (1989)]. Based on haplotype analysis, the deletion may account for most CF mutations in Northern European populations (about 68%). A second mutation is reportedly prevalent in some Southern European populations. Additional data indicate that several other mutations may cause the disease.

Studies of haplotypes of parents of CF patients (who necessarily have one normal and one disease-associated haplotype) indicated that there are at least 178 haplotypes associated with the CF locus. of those haplotypes, 90 are associated only with the disease; 78 are found only in normals; and 10 are associated with both the disease and with normals (Kerem et al. supra). The disease apparently is caused by several different mutations, some in very low frequency in the population. As demonstrated by the haplotype information, there are more haplotypes associated with the locus than there are mutant alleles responsible for the disease.

A genetic screening program (based on amplification of exon regions and analysis of the resultant amplified DNA sequence with probes specific for each of the mutations or with enzymes producing RFLP patterns characteristic of each mutation) may take years to develop. Such tests would depend on detection and characterization of each of the mutations, or at least of mutations causing about 90 to 95% or more of the cases of the disease. The alternative is to detect only 70 to 80% of the CF-associated genes. That alternative is generally considered unacceptable and is the cause of much concern in the scientific community.

The present method directly determines haplotypes associated with the locus and can detect haplotypes among the 178 currently recognized haplotypes associated with the disease locus. Additional haplotypes associated with the disease are readily determined through the rapid analysis of DNA of numerous CF patients by the methods of this invention. Furthermore, any mutations which may be associated with noncoding regulatory regions can also be detected by the method and will be identified by the screening process.

Rather than attempting to determine and then detect each defect in a coding region that causes the disease, the present method amplifies intron sequences associated with the locus to determine allelic and sub-allelic patterns. In contrast to use of mutation-specific probes where only known sequence defects can be detected, new PDLP and RFLP patterns produced by intron sequences indicate the presence of a previously unrecognized haplotype.

The same analysis can be performed for phenylalanine hydroxylase locus nutations that cause phenylketonuria and for beta-globin mutations that cause beta-thalassemia and sickle cell disease and for other loci known to be associated with a genetic disease. Furthermore, neither the mutation site nor the location for a disease gene is required to determine haplotypes associated with the disease. Amplified intron sequences in the regions of closely flanking RFLP markers, such as are known for Huntington's disease and many other inherited diseases, can provide sufficient information to screen for haplotypes associated with the disease.

Muscular dystrophy (MD) is a sex-linked disease. The disease-associated gene comprises a 2.3 million basepair sequence that encodes 3,685 amino acid protein, dystrophin. A map of mutations for 128 of 34 patients with Becker's muscular dystrophy and 160 patients with Duchenne muscular dystrophy identified 115 deletions and 13 duplications in the coding region sequence [Den Dunnen et al, Am. J. Hum. Genet. 45:835–847 (1989)]. Although the disease is associated with a large number of mutations that vary widely, the mutations have a non-random distribution in the sequence and are localized to two major mutation hot spots, Den Dunnen et al, supra. Further, a recombination hot spot within the gene sequence has been identified [Grimm et al, Am. F. Hum. Genet. 45:368–372 (1989)].

For analysis of MD, haplotypes on each side of the recombination hot spot are preferably determined. Primer pairs defining amplified DNA sequences are preferably located near, within about 1 to 10 Kbp of the hot spot on either side of the hot spot. In addition, due to the large size of the gene, primer pairs defining amplified DNA sequences are preferably located near each end of the gene sequence and most preferably also in an intermediate location on each side of the hot spot. In this way, haplotypes associated with the disease can be identified.

Other diseases, particularly malignancies, have been shown to be the result of an inherited recessive gene together with a somatic mutation of the normal gene. One malignancy that is due to such "loss of heterogeneity" is retinoblastoma, a childhood cancer. The loss of the normal gene through mutation has been demonstrated by detection of the presence of one mutation in all somatic cells (indicating germ cell origin) and detection of a second mutation in some somatic cells [Scheffer et al, Am. J. Hum. Genet. 45:252–260 (1989)]. The disease can be detected by amplifying somatic cell, genomic DNA sequences that encompass sufficient intron sequence nucleotides. The amplified DNA sequences preferably encompass intron sequences locate near one or more of the markers described by Scheffer et al, supra. Preferably, an amplified DNA sequence located near an intragenic marker and an amplified DNA sequence located near a flanking marker are used.

An exemplary analysis for CF is described in detail in the examples. Analysis of genetic loci for other monogenic and multigenic genetic diseases can be performed in a similar manner.

As the foregoing description indicates, the present method of analysis of intron sequences is generally applicable to detection of any type of genetic trait. Other monogenic and multigenic traits can be readily analyzed by the methods of the present invention. Furthermore, the analysis methods of the present method are applicable to all eukaryotic cells, and are preferably used on those of plants and animals. Examples of analysis of BOLA (bovine MHC determinants) further demonstrates the general applicability of the methods of this invention.

This invention is further illustrated by the following specific but non-limiting examples. Procedures that are constructively reduced to practice are described in the present tense, and procedures that have been carried out in the laboratory are set forth in the past tense.

EXAMPLE 1

Forensic Testing

DNA extracted from peripheral blood of the suspected perpetrator of a crime and DNA from blood found at the crime scene are analyzed to determine whether the two samples of DNA are from the same individual or from different individuals.

The extracted DNA from each sample is used to form two replicate aliquots per sample, each aliquot having 1 µg of sample DNA. Each replicate is combined in a total volume of 100 µl with a primer pair (1 µg of each primer), dNTPs (2.5 mM each) and 2.5 units of Taq polymerase in amplification buffer (50 mM KCl; 10 mM Tris-HCl, pH 8.0; 2.5 mM MgCl$_2$; 100 µg/ml gelatin) to form four amplification reaction mixtures. The first primer pair contains the primers designated SGD005.IIVS1.LNP and SGD009.AIVS3.R2NP (A locus-specific). The second primer pair contains the primers designated SGD001.DQA1.LNP and SGD003.DQA1.RNP (DQA locus-specific). Each primer is synthesized using an Applied Biosystems model 308A DNA synthesizer. The amplification reaction mixtures are designated SA (suspect's DNA, A locus-specific primers), SD (suspect's DNA, DQA1 locus-specific primers), CA (crime scene DNA, A locus-specific primers) and CD (crime scene DNA, DQA1 locus-specific primers).

Each amplification reaction mixture is heated to 94° C. for 30 seconds. The primers are annealed to the sample DNA by cooling the reaction mixtures to 65° C. for each of the A locus-specific amplification mixtures and to 55° C. for each of the DQA1 locus-specific amplification mixtures and maintaining the respective temperatures for one minute. The primer extension step is performed by heating each of the amplification mixtures to 72° C. for one minute. The denaturation, annealing and extension cycle is repeated 30 times for each amplification mixture.

Each amplification mixture is aliquoted to prepare three restriction endonuclease digestion mixtures per amplification mixture. The A locus reaction mixtures are combined with the endonucleases BsrI, Cfr101 and DraII. The DQA1 reaction mixtures are combined with AluI, CvijI and DdeI.

To produce each digestion mixture, each of three replicate aliquots of 10 µl of each amplification mixture is combined with 5 units of the respective enzyme for 60 minutes at 37° C. under conditions recommended by the manufacturer of each endonuclease.

Following digestion, the three digestion mixtures for each of the samples (SA, SD, CA and CD) are pooled and electrophoresed on a 6.5% polyacrylamide gel for 45 minutes at 100 volts. Following electrophoresis, the gel is stained with ethidium bromide.

The samples contain fragments of the following lengths:
SA: 786, 619, 596, 462, 427, 399, 256, 251, 93, 80
CA: 809, 786, 619, 596, 473, 462, 427, 399, 369, 335, 315, 283, 256, 251, 247, 93, 80
SD: 388, 338, 332, 277, 219, 194, 122, 102, 89, 79, 64, 55
CD: 587, 449, 388, 338, 335, 332, 277, 271, 219, 194, 187, 122, 102, 99, 89, 88, 79, 65, 64, 55

The analysis demonstrates that the blood from the crime scene and from the suspected perpetrator are not from the same individual. The blood from the crime scene and from the suspected perpetrator are, respectively, A3, A9, DQA1 0501, DQA1 0301 and A9, A9, DQA1 0501, DQA1 0501.

EXAMPLE 2

Paternity Testing

Chorionic villus tissue was obtained by trans-cervical biopsy from a 7-week old conceptus (fetus). Blood samples were obtained by venepuncture from the mother (M), and from the alleged father (AF). DNA was extracted from the chorionic villus biopsy, and from the blood samples. DNA was extracted from the sample from M by use of nonionic detergent (Tween 20) and proteinase K. DNA was extracted from the sample from F by hypotonic lysis. More specifically, 100 µl of blood was diluted to 1.5 ml in PBS and centrifuged to remove buffy coat. Following two hypotonic lysis treatments involving resuspension of buffy coat cells in water, the pellets were washed until redness disappeared. Colorless pellets were resuspended in water and boiled for 20 minutes. Five 10 mm chorionic villus fronds were received. One frond was immersed in 200 µl water. NaOH was added to 0.05 M. The sample was boiled for 20 minutes and then neutralized with HCl. No further purification was performed for any of the samples.

The extracted DNA was submitted to PCR for amplification of sequences associated with the HLA loci, DQA1 and DPB1. The primers used were: (1) as a 5' primer for the DQA1 locus, the primer designated SGD001.DQA1.LNP (DQA 5'IVS1) (corresponding to nt 23-39 of the DQA1 0301 allele sequence) and as the 3' primer for the DQA1 locus, the primer designated SGD003.DQA1.RNP (DQA 3'IVS2 corresponding to nt 789-806 of the DQA1 0301 sequence; (2) as the DPB primers, the primers designated 5'IVS1 nt 7604-7624 and 3'IVS2 7910-7929. The amplification reaction mixtures were: 150 ng of each primer; 25 µ of test DNA; 10 mM Tris HCl, pH 8.3; 50 mM KCl; 1.5 mM $MgCl_2$; 0.01% (w/v) gelatin; 200 µM dNTPs; water to 100 µl and 2.5 U Taq polymerase.

The amplification was performed by heating the amplification reaction mixture to 94° C. for 10 minutes prior to addition of Taq polymerase. For DQA1, the amplification was performed at 94° C. for 30 seconds, then 55° C. for 30 seconds, then 72° C. for 1 minute for 30 cycles, finishing with 72° C. for 10 minutes. For DPB, the amplification was performed at 96° C. for 30 seconds, then 65° C. for 30 seconds, finishing with 65° C. for 10 minutes.

Amplification was shown to be technically satisfactory by test gel electrophoresis which demonstrated the presence of double stranded DNA of the anticipated size in the amplification reaction mixture. The test gel was 2% agarose in TBE (tris borate EDTA) buffer, loaded with 15 µl of the amplification reaction mixture per lane and electrophoresed at 200 v for about 2 hours until the tracker dye migrated between 6 to 7 cm into the 10 cm gel.

The amplified DQA1 and DPB1 sequences were subjected to restriction endonuclease digestion using DdeI and MboII (8 and 12 units, respectively at 37° C. for 3 hours) for DQA1, and RsaI and FokI (8 and 11 units, respectively at 37° C. overnight) for DPB1 in 0.5 to 2.0 µl of enzyme buffers recommended by the supplier, Pharmacia together with 16–18 µl of the amplified product. The digested DNA was fragment size-length separated on gel electrophoresis (3% Nusieve). The RFLP patterns were examined under ultraviolet light after staining the gel with ethidium bromide.

Fragment pattern analysis is performed by allele assignment of the non-maternal alleles using expected fragment sizes based on the sequences of known endonuclease restriction sites. The fragment pattern analysis revealed the obligate paternal DQA1 allele to be DQA1 0102 and DPB to be DPw1. The fragment patterns were consistent with AF being the biological father.

To calculate the probability of true paternity, HLA types were assigned. Maternal and AF DQA1 types were consistent with those predicted from the HLA Class II gene types determined by serological testing using lymphocytotoxic antisera.

Considering alleles of the two HLA loci as being in linkage equilibrium, the combined probability of non-paternity was given by:

$$0.042 \times 0.314 - 0.013$$

i.e. the probability of paternity is (1–0.013) or 98.7%.

The relative chance of paternity is thus 74:75, i.e. the chance that the AF is not the biological father is approximately 1 in 75. The parties to the dispute chose to regard these results as confirming the paternity of the fetus by the alleged father.

EXAMPLE 3

Analysis of the HLA DQA1 Locus

The three haplotypes of the HLA DQA1 0102 locus were analyzed as described below. Those haplotypes are DQA1 0102 DR15 Dw2; DQA1 0102 DR16 Dw21; and DQA1 0102 DR13 Dw19. The distinction between the haplotypes is particularly difficult because there is a one basepair difference between the 0102 alleles and the 0101 and 0103 alleles, which difference is not unique in DQA1 allele sequences.

The procedure used for the amplification is the same as that described in Example 1, except that the amplification used thirty cycles of 94° C. for 30 seconds, 60° C. for 30 seconds, and 72° C. for 60 seconds. The sequences of the primers were:

SGD 001- 5' TTCTGAGCCAGTCCTGAGA 3'; and
SGD 003 -5' GATCTGGGGACCTCTTGG 3'.

These primers hybridize to sequences about 500 bp upstream from the 5' end of the second exon and 50 bp downstream from the second exon and produce amplified DNA sequences in the 700 to 800 bp range.

Following amplification, the amplified DNA sequences were electrophoresed on a 4% polyacrylamide gel to determine the PDLP type. In this case, amplified DNA sequences for 0102 comigrate with (are the same length as) 0101 alleles and subsequent enzyme digestion is necessary to distinguish them.

The amplified DNA sequences were digested using the restriction enzyme AluI (Bethesda Research Laboratories) which cleaves DNA at the sequence AGCT. The digestion was performed by mixing 5 units (1 μl) of enzyme with 10 μl of the amplified DNA sequence (between about 0.5 and 1 μg of DNA) in the enzyme buffer provided by the manufacturer according to the manufacturer's directions to form a digest. The digest was then incubated for 2 hours at 37° C. for complete enzymatic digestion.

The products of the digestion reaction are mixed with approximately 0.1 μg of "ladder" nucleotide sequences (nucleotide control sequences beginning at 123 bp in length and increasing in length by 123 bp to a final size of about 5,000 bp; available commercially from Bethesda Research Laboratories, Bethesda MD) and were electrophoresed using a 4% horizontal ultra-thin polyacrylamide gel (E-C Apparatus, Clearwater FLA). The bands in the gel were visualized (stained) using silver stain technique [Allen et al. *BioTechniques* 7:736–744 (1989)].

Three distinctive fragment patterns which correspond to the three haplotypes were produced using AluI. The patterns (in base pair sized fragments) were:

1. DR15 DQ6 Dw2: 120, 350, 370, 480
2. DR13 DQ6 Dw19: 120, 330, 350, 480
3. DR16 DQ6 Dw21: 120, 330, 350

The procedure was repeated using a 6.5% vertical polyacrylamide gel and ethidium bromide stain and provided the same results. However, the fragment patterns were more readily distinguishable using the ultrathin gels and silver stain.

This exemplifies analysis according to the method of this invention. Using the same procedure, 20 of the other 32 DR/DQ haplotypes for DQA1 were identified using the same primer pair and two additional enzymes (DdeI and MboII). PDLP groups and fragment patterns for each of the DQA1 haplotypes with the three endonucleases are illustrated in Table 6.

| PDLP | DR | Dw | 480 | 410 | 405 | 400 | 390 | 370 | 360 | 350 | 340 | 330 | 310 | 300 | 270 | 240 | 120 | 110 | 100 |
|---|---|---|---|---|---|---|---|---|---|---|---|---|---|---|---|---|---|---|---|
| | | | | | | | | AluI | | | | | | | | | | | |
| 0101 | 1 | 1 | | | | | | | | | | | + | + | | | + | | |
| | 1 | 20 | | | | | | | | | | | + | + | | | + | | |
| | 14 | 9 | | | | | | | | | | | + | + | | | + | | |
| 0102 | 15 | 2 | + | | | | | + | | + | | | | | | | + | | |
| | 16 | 21 | | | | | | | | + | + | | | | | | + | | |
| | 13 | 19 | + | | | | | | | + | + | | | | | | + | | |
| 0103 | 13 | 18, 24 | | | | | | | | | | | | | | | | | |
| | 13 | 18, 25 | | | | | | | | | | | + | | + | | + | | |
| | 8 | 8.3 | | | | | | | | + | | + | | | | | + | | + |
| | 11 | DB2 | | | | | | | | | | | | | | | | | |
| | 15 | 12 | | | | | | | | | | | | | | | | | |
| 0201 | 7 | DB1 | | | | | + | | | | | | | | + | | | | |
| | 7 | 17 | | | | | + | | | | | | | | + | | | | |
| | 7 | 11 | | | | | | + | | | + | | | | | | | | |
| 0301 | 4 | 4 (7) | | | | | | | | | | | | | | | | | |
| | 4 | 13.2 (7) | | | | | | | | | | | | | | | | | |
| | 4 | 4 (8) | | | | | + | | | + | | | | | | | | | |
| | 4 | 10 (8) | | | | | + | | | + | | | | | | | | | |
| | 4 | 13.1 (8) | | | | | | | | | | | | | | | | | |
| | 4 | 14 (8) | | | | | + | | | + | | | | | | | | | |
| | 4 | KT2 | | | | | | | | | | | | | | | | | |
| | 4 | 15 | | | | | | | | | | | | | | | | | |
| | 9 | 23 | | | | + | | | + | | | | | | | | | | |
| 0401 | 8 | 8.1 | | (+) | | | | | | | | | + | | | + | + | + | |
| | 8 | 8.2 | | (+) | | | | | | | | | + | | | + | + | + | |
| | 3 | RSH | | | | | | | | | | | | | | | | | |
| 0501 | 3 | 3, 24 | | (+) | | | | | | | | | + | | | | + | | |
| | 3 | 3, 25 | | (+) | | | | | | | | | + | | | | + | | |
| | 11 | 5 | | (+) | | | | | | | | | + | | | | + | | |
| | 11 | 5 (9104) | + | | | | | | | | | | + | | | | + | | |
| | 14 | 16 | | (+) | | | | | | | | | + | | | | + | | |
| | 12 | DB6 | | (+) | | | | | | | | | + | | | | + | | |
| | 16 | 22 | | | | | | | | | | | | | | | | | |
| 0601 | 8 | 8.3 | | (+) | | | | | | | | | + | | | | + | | |
| PDLP | DR | Dw | 480 | 410 | 405 | 400 | 390 | 370 | 360 | 350 | 340 | 330 | 310 | 300 | 270 | 240 | 120 | 110 | 100 |

| PDLP | DR | Dw | DdeI | | | | | | | | | | | | | |
|---|---|---|---|---|---|---|---|---|---|---|---|---|---|---|---|---|
| | | | 650 | 520 | 450 | 420 | 410 | 400 | 390 | 300 | 200 | 190 | 150 | 90 | 80 | 60 | 50 |
| 0101 | 1 | 1 | | | | + | | | | | | | + | | + | + | |
| | 1 | 20 | | | | + | | | | | | | + | | + | + | |
| | 14 | 9 | | | | + | | | | | | | + | | + | + | |
| 0102 | 15 | 2 | | + | | + | | | | | | | + | | + | + | |
| | 16 | 21 | | | | + | | | | | | | + | | + | + | |
| | 13 | 19 | | | | | + | | | | | | + | | + | + | |
| 0103 | 13 | 18, 24 | | | | | | | | | | | | | | | |
| | 13 | 18, 25 | | | | | | | | | | | | | | | |
| | 8 | 8.3 | | | | + | | | | | | | + | | + | | + |
| | 11 | DB2 | | | | | | | | | | | | | | | |
| | 15 | 12 | | | | | | | | | | | | | | | |
| 0201 | 7 | DB1 | | | | | | + | | | | | + | | + | | + |
| | 7 | 17 | | | | | | | | | | | + | | + | | + |
| | 7 | 11 | | | | | | + | | | | | + | | + | | + |
| 0301 | 4 | 4 (7) | | | | | | | | | | | | | | | |
| | 4 | 13.2 (7) | | | | | | | | | | | | | | | |
| | 4 | 4 (8) | + | | | | | | | | | | | + | | | + |
| | 4 | 10 (8) | + | | | | | | | | | | | + | | | + |
| | 4 | 13.1 (8) | | | | | | | | | | | | | | | |
| | 4 | 14 (8) | + | | | | | | | | | | | + | | | + |
| | 4 | KT2 | | | | | | | | | | | | | | | |
| | 4 | 15 | | | | | | | | | | | | | | | |
| | 9 | 23 | + | | | | | | | | | | | + | | | + |
| 0401 | 8 | 8.1 | | | | | | | | | + | + | | + | + | | + |
| | 8 | 8.2 | | | | | | | | | + | + | | + | + | | + |
| | 3 | RSH | | | | | | | | | | | | | | | |
| 0501 | 3 | 3, 24 | | | | | | + | | | + | | | | + | | + |
| | 3 | 3, 25 | | | | | | + | | | + | | | | + | | + |
| | 11 | 5 | | | | | | + | | | + | | | | + | | + |
| | 11 | 5 (9104) | | | | | | + | | | + | | + | | + | | + |
| | 14 | 16 | | | | | | | + | | + | | | | + | | + |
| | 12 | DB6 | | | | | | + | | | + | | | | + | | + |
| | 16 | 22 | | | | | | | | | | | | | | | |
| 0601 | 8 | 8.3 | | | | | | | | + | + | | | + | + | | + |
| PDLP | DR | Dw | 650 | 520 | 450 | 420 | 410 | 400 | 390 | 300 | 200 | 190 | 150 | 90 | 80 | 60 | 50 |

| PDLP | DR | Dw | MboII | | | | | | | | | | | | | | | | | | |
|------|----|----|-------|---|---|---|---|---|---|---|---|---|---|---|---|---|---|---|---|---|---|
| | | | 390 | 385 | 380 | 370 | 365 | 360 | 350 | 340 | 335 | 330 | 305 | 300 | 250 | 190 | 180 | 170 | 140 | 130 |
| 0101 | 1 | 1 | | | | | | | + | | | | | | | | | | | |
| | 1 | 20 | | | | | | | + | | | | | + | | | | | | |
| | 14 | 9 | | | | | | | | | | | | + | | | | | | |
| 0102 | 15 | 2 | | | | + | | | | | | | | + | | | | | | |
| | 16 | 21 | | | | + | | | | | | | + | | | | | | | |
| | 13 | 19 | | | | + | | | | | | | | + | | | | | | |
| 0103 | 13 | 18, 24 | | | | | | | | | | | | | | | | | + | |
| | 13 | 18, 25 | | | | | | + | | | | | | | | + | | | + | |
| | 8 | 8.3 | | | | | | + | | | | | | | | + | | | | |
| | 11 | DB2 | | | | | | | | | | | | | | | | | | |
| | 15 | 12 | | | | | | | | | | | | | | | | | | |
| 0201 | 7 | DB1 | | | | | | | + | | | | | | | | | + | | + |
| | 7 | 17 | | | | | | | + | | | | | | | | | + | | + |
| | 7 | 11 | | | | | | | + | | | | | | | | | | | + |
| 0301 | 4 | 4 (7) | | | | | | | | | | | | | | | | | | |
| | 4 | 13.2 (7) | | | | | | | | | | | | | | | | | | |
| | 4 | 4 (8) | | | | | | | | | | | | | + | | | + | | |
| | 4 | 10 (8) | | | | | | | | | | | | | + | | + | + | | |
| | 4 | 13.1 (8) | | | | | | | | | | | | | | | | + | | |
| | 4 | 14 (8) | | | | | | | | | | | | | | | + | + | | |
| | 4 | KT2 | | | | | | | | | | | | | | + | | + | | |
| | 4 | 15 | | | | | | | | | | | | | | | | | | |
| | 9 | 23 | | | | | | | | | + | | | | | | | | | |
| 0401 | 8 | 8.1 | | | | | + | + | | | | + | | | | | | | | |
| | 8 | 8.2 | | | | | + | | | + | | | | | | | | | | |
| | 3 | RSH | | | | | | | | + | | | | | | | | | | |
| 0501 | 3 | 3, 24 | + | | + | | | | | + | | | | | | | | | | |
| | 3 | 3, 25 | + | | + | | | | | + | | | | | | | | | | |
| | 11 | 5 | | | + | | | | | | | | | | | | | | | |
| | 11 | 5 (9104) | | + | | | | | | | | | | | | | | | + | |
| | 14 | 16 | + | | | | | | | | | | + | | | | | | | + |
| | 12 | DB6 | | | | | | | | | | | | | | | | | | |
| 0601 | 16 | 22 | | | | | | | | | | | | | | | | | | |
| | 8 | 8.3 | | | | | | | | | | | + | | | | | | | |
| PDLP | DR | Dw | 390 | 385 | 380 | 370 | 365 | 360 | 350 | 340 | 335 | 330 | 305 | 300 | 250 | 190 | 180 | 170 | 140 | 130 |

This example illustrates the ability of the method of this invention to distinguish the alleles and haplotypes of a genetic locus. Specifically, the example shows that PDLP analysis stratifies five of the eight alleles. These three restriction endonuclease digests distinguish each of the eight alleles and many of the 35 known haplotypes of the locus. The use of additional endonuclease digests for this amplified DNA sequence can be expected to distinguish all of the known haplotypes and to potentially identify other previously unrecognized haplotypes. Alternatively, use of the same or other endonuclease digests for another amplified DNA sequence in this locus can be expected to distinguish the haplotypes.

In addition, analysis of amplified DNA sequences at the DRA locus in the telomeric direction and DQB in the centromeric direction, preferably together with analysis of a central locus, can readily distinguish all of the haplotypes for the region.

The same methods are readily applied to other loci.

EXAMPLE 4

Analysis of the HLA DQA1 Locus

The DNA of an individual is analyzed to determine which of the three haplotypes of the HLA DQA1 0102 locus are present. Genomic DNA is amplified as described in Example 3. Each of the amplified DNA sequences is sequenced to identify the haplotypes of the individual. The individual is shown to have the haplotypes DR15 DQ6 Dw2; DR13 DQ6 Dw19.

The procedure is repeated as described in Example 3 through the production of the AluI digest. Each of the digest fragments is sequenced. The individual is shown to have the haplotypes DR15 DQ6 Dw2; DR13 DQ6 Dw19.

EXAMPLE 5

DQA1 Allele-Specific Amplification

Primers were synthesized that specifically bind the 0102 and 0301 alleles of the DQA1 locus. The 5' primer was the SGD 001 primer used in Example 3. The sequences of the 3' primers are listed below.

0102 5' TTGCTGAACTCAGGCCACC 3'
0301 5' TGCGGAACAGAGGCAACTG 3'

The Amplification was Performed as Described in Example 3 using 30 cycles of a standard (94° C., 60° C., 72° C.) PCR reaction. The template DNAs for each of the 0101, 0301 and 0501 alleles were amplified separately. As determined by gel electrophoresis, the 0102-allele-specific primer amplified only template 0102 DNA and the 0301-allele-specific primer amplified only template 0301 DNA. Thus, each of the primers was allele-specific.

EXAMPLE 6

Detection of Cystic Fibrosis

The procedure used for the amplification described in Example 3 is repeated. The sequences of the primers are illustrated below. The first two primers are upstream primers, and the third is a downstream primer. The primers amplify a DNA sequence that encompasses all of intervening sequence 1

5' AG AGG TCG CCT CTG GA-3';
5' AAG GCC AGC GTT GTC TCC A 3'; and
3' CT CAA AAT TGG TCT GGT 5'.

These primers hybridize to the complement of sequences located from nt 136-152 and nt 154-172, and to nt 187-207. [The nucleotide numbers are found in Riordan et al. *Science* 245:1066–1072 (1989).]

Following amplification, the amplified DNA sequences are electrophoresed on a 4% polyacrylamide gel to determine the PDLP type. The amplified DNA sequences are separately digested using each of the restriction enzymes AluI, MnlI and RsaI (Bethesda Research Laboratories). The digestion is performed as described in Example 3. The products of the digestion reaction are electrophoresed and visualized using a 4% horizontal ultra-thin polyacrylamide gel and silver stain as described in Example 3.

Distinctive fragment patterns which correspond to disease-associated and normal haplotypes are produced.

EXAMPLE 7

Analysis of Bovine HLA Class I

Bovine HLA Class I alleles and haplotypes are analyzed in the same manner as described in Example 3. The primers are listed below.

| Bovine Primers (Class I HLA homolog) | | $T_m$ |
|---|---|---|
| 5' primer: | 5' TCC TGG TCC TGA CCG AGA 3' | (62°) |
| 3' primer: | 1) 3' A TGT GCC TTT GGA GGG TCT 5' (for ⁻600 bp product) | (62°) |
| | 2) 3' GCC AAC AT GAT CCG CAT 5' (for ~900 bp product) | (62°) |

For the approximately 900 bp sequence PDLP analysis is sufficient to distinguish alleles 1 and 3 (893 and 911 bp, respectively). Digests are prepared as described in Example 3 using AluI and DdeI. The following patterns are produced for the 900 bp sequence.

Allele 1, AluI digest: 712, 181
Allele 3, AluI digest: 430, 300, 181
Allele 1, DdeI digest: 445, 201, 182, 28
Allele 3, DdeI digest: 406, 185, 182, 28, 16

The 600 bp sequence also produces distinguishable fragment patterns for those alleles. However, those patterns are not as dramatically different as the patterns produced by the 600 bp sequence digests.

EXAMPLE 8

Preparation of Primers

Each of the following primers is synthesized using an Applied Biosystems model 308A DNA synthesizer.

HLA Locus Primers
A Locus-Specific Primers
SGD009.AIVS3.R2NP  CATGTGGCCATCT-
    TGAGAATGGA
SGD006.AIVS3.R1NP  GCCCGGGAGATCTACAGGC-
    GATCA
A2.1 CGCCTCCCTGATCGCCTGTAG
A2.2 CCAGAGAGTGACTCTGAGG
A2.3 CACAATTAAGGGAT
B Locus-Specific Primers
SGD007.BIVS3.R1NP  TCCCCGGCGACCTATAG-
    GAGATGG
SGD010.BIVS3.R2NP  CTAGGACCACCCATGTGAC-
    CAGC
B2.1 ATCTCCTCAGACGCCGAGATGCGTCAC
B2.2 CTCCTGCTGCTCTGGGGGGCAG B2.3 ACTTTACCTCCACTCAGATCAGGAG
D2.4 CGTCCAGGCTGGTGTCTGGGTTCTGTGCCCCT
B2.5 CTGGTCACATGGGTGGTCCTAGG
B2.6 CGCCTGAATTTTCTGACTCTTCCCAT
C Locus-Specific Primners
SGD008.CIVS3.R1NP ATCCCGGGAGATCTACAG-GAGATG
SGD011. CIVS3.R2NP AACAGCGCCCATGTGAC-CATCCT
C2.1 CTGGGGAGGCGCCGCGTTGAGGATTCT
C2.2 CGTCTCCGCAGTCCCGGTTCTAAAGTTC-CCAGT
C2.3 ATCCTCGTGCTCTCGGGA
C2.4 TGTGGTCAGGCTGCTGAC
C2.5 AAGGTTTGATTCCAGCTT
C2.6 CCCCTTCCCCACCCCAGGTGTTCCTGTC-CATTCTTCAGGA
C2.7 CACATGGGCGCTGTTGGAGTGTCG
Class I Loci-Specific Primers
SGD005.IIVS1.LNP GTGAGTGCGGGGTCGGGAGGGA
1.1 CACCCACCGGGACTCAGA
1.2 TGGCCCTGACCCAGACCTGGGC
1.3 GAGGGTCGGGCGGGTCTCAGC
1.4 CTCTCAGGCCTTGTTC
1.5 CAGAAGTCGCTGTTCC
DQA1 Locus-Specific Primers
SGD001.DQA1.LNP TTCTGAGCCAGTCCTGAGA
DQA3 E1a TTGCCCTGACCACCGTGATG
DQA3 E1b CTTCCTGCTTGTCATCTTCA
DQA3 E1c CCATGAATTTGATGGAGA
DQA3 E1d ACCGCTGCTACCAATGGTA
SGD003.DQA1.RNP CCAAGAGGTCCCCAGATC
DRA Locus-Specific Primers
DRA E1 TCATCATAGCTGTGCTGATG
DRA 5'E2 AGAACATGTGATCATCCAGGC
DRA 3'E2 CCAACTATACTCCGATCACCAAT
DRB Locus-Specific Primers
DRB E1 TGACAGTGACACTGATGGTGCTG
DRB 5'E2 GGGGACACCCGACCACGTTTC
DRB 3'E2 TGCAGACACAACTACGGGGTTG
DOB1 Locus-Specific Primers
DQB E1 TGGCTGAGGGCAGAGACTCTCCC
DQB 5'E2 TGCTACTTCACCAACGGGAC
DQB 3'E2 GGTGTGCACACACAACTAC
DQB 5'IVS1a AGGTATTTTACCCAGGGACCAAGAGAT
DQB 5'IVS1b ATGTAAAATCAGCCCGACTGCCTCTTC
DQB 3'IVS2 GCCTCGTGCCTTATGCGTTTGCCTCCT
DPB1 Locus-Specific Primers
DPB E1 TGAGGTTAATAAACTGGAGAA

DPB 5'IVS1 GAGAGTGGCGCCTCCGCTCAT
DPB 3'IVS2 GAGTGAGGGCTTTGGGCCGG

What is claimed is:

1. An HLA locus-specific primer wherein said primer hybridizes with a portion of the stated gene locus or its complementary strand and does not hybridize with other DNA sequences under the conditions used in an amplification method, and wherein said primer has a sequence corresponding to at least 14 consecutive nucleotides selected from the group consisting of CATGTGGCCATCT-TGAGAATGGA; GCCCGGGAGATCTACAGGCGATCA; CGCCTCCCTGATCGCCTGTAG; CCAGAGAGT-GACTCTGAGG; CACAATTAAGGGAT; TCCCCGGC-GACCTATAGGAGATGG; CTAGGACCACCCAI; GTGACCAGC; ATCTCCTCAGACGCCGAGATGCGT-CAC; CTCCTGCTGCTCTGGGGGCAG; ACTTTAC-CTCCACTCAGATCAGGAG; CGTCCAGGCTGGT-G T C T G G G T T C T G T G C C C C T ; CTGGTCACATGGGTGGTCCTAGG; CGCCT-GAATTTTCTGACTCTTCCCAT; ATCCCGGGAGATC-TACAGGAGATG; AACAGCGCCCATGTGACCATCCT; CTGGGGAGGCGCCGCGTTGAGGATTCT; CGTCTC-CGCAGTCCCGGTTCTAAAGTTCCCAGT; ATCCTCGT-GCTCTCGGGA; TGTGGTCAGGCTGCTGAC; AAG-G T T T G A T T C C A G C T T ; CCCCTTCCCCACCCCAGGTGTTCCTGTC-CATTCTTCAGGA; CACATGGGCGCTGTTGGAGT-GTCG; GTGAGTGCGGGGTCGGGAGGGA; CAC-C C A C C G G G A C T C A G A ; T G G C C C T G A C C C A G A C C T G G G C ; GAGGGTCGGGCGGGTCTCAGC; CTCTCAGGCCT-TGTTC; CAGAAGTCGCTGTTCC; TTCTGAGCC-CAGTCCTGAGA; TTGCCCTGACCACCGTGATG; CTTCCTGCTTGTCATCTTCA; CCATGAATTTGATG-GAGA; ACCGCTGCTACCAATGGTA; CCAAGAGGTC-CCCAGATC; TCATCATAGCTGTGCTGATG; AGAA-C A T G T G A T C A T C C A G G C ; CCAACTATACTCCGATCACCAAT; TGACAGTGA-CACTGATGGTGCTG; GGGGACACCCGAC-CACGTTTC; TGCAGACACAACTACGGGGTTG; TGGCTGAGGGCAGAGACTCTCCC; TGCTACTTCAC-CAACGGGAC; GGTGTGCACACACAACTAC; AGG-TATTTTACCCAGGGACCAAGAGAT; ATGTAAAAT-C A G C C C G A C T G C C T C T T C ; GCCTCGTGCCTTATGCGTTTGCCTCCT; TGAGGT-TAATAAACTGGAGAA; GAGAGTGGCGCCTCCGCT-CAT; and GAGTGAGGGCTTTGGGCCGG.

* * * * *